United States Patent
Abe et al.

(10) Patent No.: US 8,483,466 B2
(45) Date of Patent: Jul. 9, 2013

(54) MAGNETIC RESONANCE IMAGING APPARATUS AND BLOOD VESSEL IMAGE ACQUIRING METHOD

(75) Inventors: Takayuki Abe, Tokyo (JP); Tetsuhiko Takahashi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 241 days.

(21) Appl. No.: 12/991,561

(22) PCT Filed: May 18, 2009

(86) PCT No.: PCT/JP2009/059118
§ 371 (c)(1),
(2), (4) Date: Nov. 8, 2010

(87) PCT Pub. No.: WO2009/142167
PCT Pub. Date: Nov. 26, 2009

(65) Prior Publication Data
US 2011/0064294 A1    Mar. 17, 2011

(30) Foreign Application Priority Data
May 22, 2008   (JP) .................. 2008-133732

(51) Int. Cl.
   *G06K 9/00*   (2006.01)
(52) U.S. Cl.
   USPC ........................................................ 382/131
(58) Field of Classification Search
   None
   See application file for complete search history.

(56) References Cited

U.S. PATENT DOCUMENTS

| | | | | |
|---|---|---|---|---|
| 4,942,359 A * | 7/1990 | Sano et al. | ..................... | 324/309 |
| 5,031,624 A * | 7/1991 | Mistretta et al. | .............. | 600/419 |
| 5,897,496 A * | 4/1999 | Watanabe | ..................... | 600/413 |
| 5,929,637 A * | 7/1999 | Taguchi et al. | ................ | 324/306 |
| 6,141,578 A * | 10/2000 | Hardy | ............................ | 600/410 |
| 6,442,414 B1 * | 8/2002 | Watanabe | ..................... | 600/419 |
| 6,954,067 B2 * | 10/2005 | Mistretta | ...................... | 324/307 |
| 2008/0161678 A1 * | 7/2008 | Miyazaki et al. | ............. | 600/419 |

FOREIGN PATENT DOCUMENTS

| | | |
|---|---|---|
| JP | 3-47236 | 2/1991 |
| JP | 4-269943 | 9/1992 |
| JP | 8-117204 | 5/1996 |
| JP | 8-140960 | 6/1996 |
| JP | 9-220212 | 8/1997 |
| JP | 11-244257 | 9/1999 |
| JP | 2001-70279 | 3/2001 |
| JP | 2001-070279 | * 3/2001 |
| JP | 2006-130116 | 5/2006 |

OTHER PUBLICATIONS

JP 2001-070279 Computer translation Mar. 21, 2001.*
International Search Report in JP/PCT2009/059118.

* cited by examiner

*Primary Examiner* — Chan S. Park
*Assistant Examiner* — Nancy Bitar
(74) *Attorney, Agent, or Firm* — Cooper & Dunham LLP

(57) ABSTRACT

Plural blood vessels different in blood flow velocity are depicted with high image quality in blood vessel imaging using PC-MRA method. For this purpose, the present invention performs a measurement of an echo signal based on application of a positive-polarity flow encode pulse and a measurement of an echo signal based on application of a negative-polarity flow encode pulse on an examinee with each of plural phase encodes while varying the flow encode, and a blood vessel image of the examinee is reconstructed by using the plural echo signals having different flow encode absolute values.

14 Claims, 17 Drawing Sheets

FIG. 4

| | FH DIRECTION | AP DIRECTION | RL DIRECTION |
|---|---|---|---|
| FIRST (1) | + | + | - |
| SECOND (2) | + | - | + |
| THIRD (3) | - | + | + |
| FOURTH (4) | - | - | - |

+ : POSITIVE POLARITY (301 OF FIG. 3)
- : NEGATIVE POLARITY (302 OF FIG. 3)

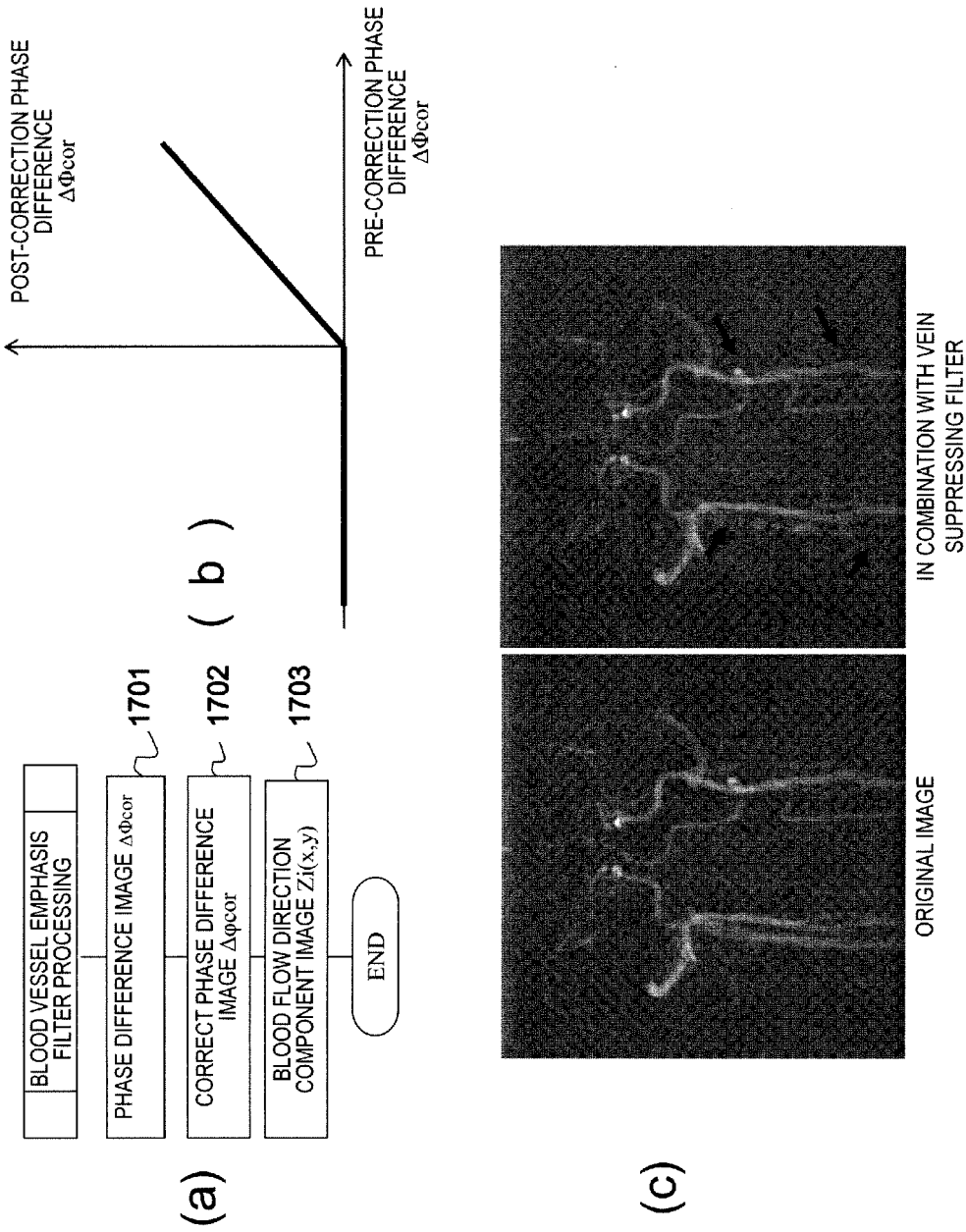

MAGNETIC RESONANCE IMAGING APPARATUS AND BLOOD VESSEL IMAGE ACQUIRING METHOD

TECHNICAL FIELD

The present invention relates to a blood vessel imaging technique based on a phase contrast angiography in a nuclear magnetic resonance imaging expression g (hereinafter referred to as "MRI") device for imaging a density distribution and a relaxation time distribution of nucleus by measuring a nuclear magnetic resonance (hereinafter referred to as "NMR") signal from hydrogen, phosphorus or the like in an examinee.

BACKGROUND ART

An MRI device is a device for measuring NMR signals (echo signals) generated by atomic nucleus spins constituting an examinee, particularly a tissue of a human body, and two-dimensionally or three-dimensionally imaging the shape or function of a cephalic part, an abdominal part, four limbs or the like of the examinee. In the imaging operation, echo signals are added with different phase encodes by gradient magnetic field, subjected to frequency encoding and measured as time-series data. The measured echo signals are subjected to two-dimensional or three-dimensional Fourier Transform to be reconstructed into an image.

There is an imaging function called as MR angiography (hereinafter abbreviated to MRA) for depicting a blood vessel by using this MRI device. The MRA imaging function includes a phase contrast MRA (hereinafter referred to as PC-MRA) method for imaging blood in a blood vessel by using the principle that transverse magnetization phase of blood is shifted in accordance with blood stream rate. According to the PC-MRA method, the complex difference is taken between an image acquired by applying a positive-polarity flow encode pulse and an image acquired by applying a negative-polarity flow encode pulse, thereby obtaining a blood vessel image reflecting a flow velocity value.

According to the PC-MRA method described above, only one type of flow encode which is optimally matched with the average flow velocity of a blood vessel as an imaging target is normally set to depict the target blood vessel. For example, when a cervical part area is subjected to blood vessel imaging by the PC-MRA method, the cervical part area contains right and left carotid arteries, right and left arteria vertebralis, arteria basilaris, etc. as main blood vessels, and the flow encode is set in conformity with the average flow velocity of 40 cm/s of the carotid arteries as large blood vessels of the cervical part.

However, in general, plural blood vessels having average velocities which are different from that of a blood vessel as an imaging target exist in an area to be imaged. Therefore, in the PC-MRA method using only one type of flow encode, the target blood vessel is depicted with high brightness, however, the other blood vessels are depicted with low brightness, so that all the blood vessels different in blood stream rate do not become blood vessel images which are depicted with high brightness.

Therefore, (patent document 1) discloses a blood vessel imaging technique that the flow encode is set to a relatively small flow encode when data of low frequency components at a phase encode step are collected and set to a relatively large flow encode when data of high frequency components at the phase encode step are collected, whereby both of a main blood vessel which has a relatively high flow velocity and is large in diameter and a peripheral blood vessel which has a relatively low flow velocity and is small in diameter can be excellently depicted.

PRIOR ART DOCUMENT

Patent Document

Patent Document 1: JP-A-5-207982
Patent Document 2: U.S. Pat. No. 4,714,081

SUMMARY OF THE INVENTION

Problem to be Solved by the Invention

However, in the technique disclosed in the (patent document 1), K-space data of each flow encode are not perfectly gotten lined up. That is, with respect to K-space data associated with a relatively small flow encode, high frequency components at a phase encode step lack, and also with respect to K-space data associated with a relatively large flow encode, low frequency components at the phase encode step lack. Therefore, it is estimated that a main blood vessel which is relatively high in flow velocity and large in diameter is blurred and the brightness of a peripheral blood vessel which is relatively low in flow velocity and small in diameter is reduced, so that the image quality of each blood vessel is reduced irrespective of the flow velocity.

Therefore, the present invention has been implemented to solve the foregoing problem, and has an object to provide an MRI device and a blood vessel image acquisition method that can depict plural blood vessels different in blood stream rate with high image quality in blood vessel imaging using a PC-MRA method.

Means of Solving the Problem

In order to attain the above object, the present invention measures each of echo signals having different flow encode absolute values on the basis of each of plural phase encodes, and reconstructs a resultant image of an examinee by using the echo signals having the different flow encode absolute values.

Specifically, the MRI device according to the present invention is characterized by comprising: a measurement controller for subjecting an examinee to a measurement of an echo signal based on application of a positive-polarity flow encode pulse and a measurement of an echo signal based on application of a negative-polarity flow encode pulse in accordance with a predetermined flow encode by using plural phase encodes; and a calculation processor for reconstructing a blood vessel image of the examinee by using the echo signal based on the application of the positive-polarity flow encode pulse and the echo signal based on the application of the negative-polarity flow encode pulse, wherein the measurement controller performs a measurement of plural echo signals having different flow encode absolute values on the basis of the plural phase encodes, and the calculation processor reconstructs the blood vessel image by using the plural echo signals having the different flow encode absolute values.

Furthermore, a blood vessel image acquiring method according to the invention is characterized by comprising: subjecting an examinee to a measurement of an echo signal based on application of a positive-polarity flow encode pulse and a measurement of an echo signal based on application of a negative-polarity flow encode pulse in accordance with each flow encode on the basis of plural phase encodes while the absolute value of the flow encode is varied; and reconstructing a blood vessel image of the examinee by using the measured plural echo signals.

Effect of the Invention

According to the MRI device and the blood vessel image acquiring method of the present invention, in blood vessel imaging using a PC-MRA method, plural echo signals having different flow encode absolute values are measured by each of plural phase encodes, and the blood vessel image is reconstructed by using the echo signals. Therefore, plural blood vessels which are different in blood stream rate can be depicted with high image quality.

BRIEF DESCRIPTION OF DRAWINGS

FIG. 4 is a diagram showing a combination pattern of a flow encode pulse when blood streams in three directions are measured.

FIG. 17 is a diagram showing a second example of a vein suppressing filter according to the fourth embodiment of the present invention, wherein (a) is a flowchart showing a processing flow of vein suppressing filter processing, (b) is a diagram showing an example of the vein suppressing filter processing, and (c) is a diagram showing an effect of a blood vessel emphasizing filter.

EMBODIMENTS FOR CARRYING OUT THE INVENTION

Figure 1:
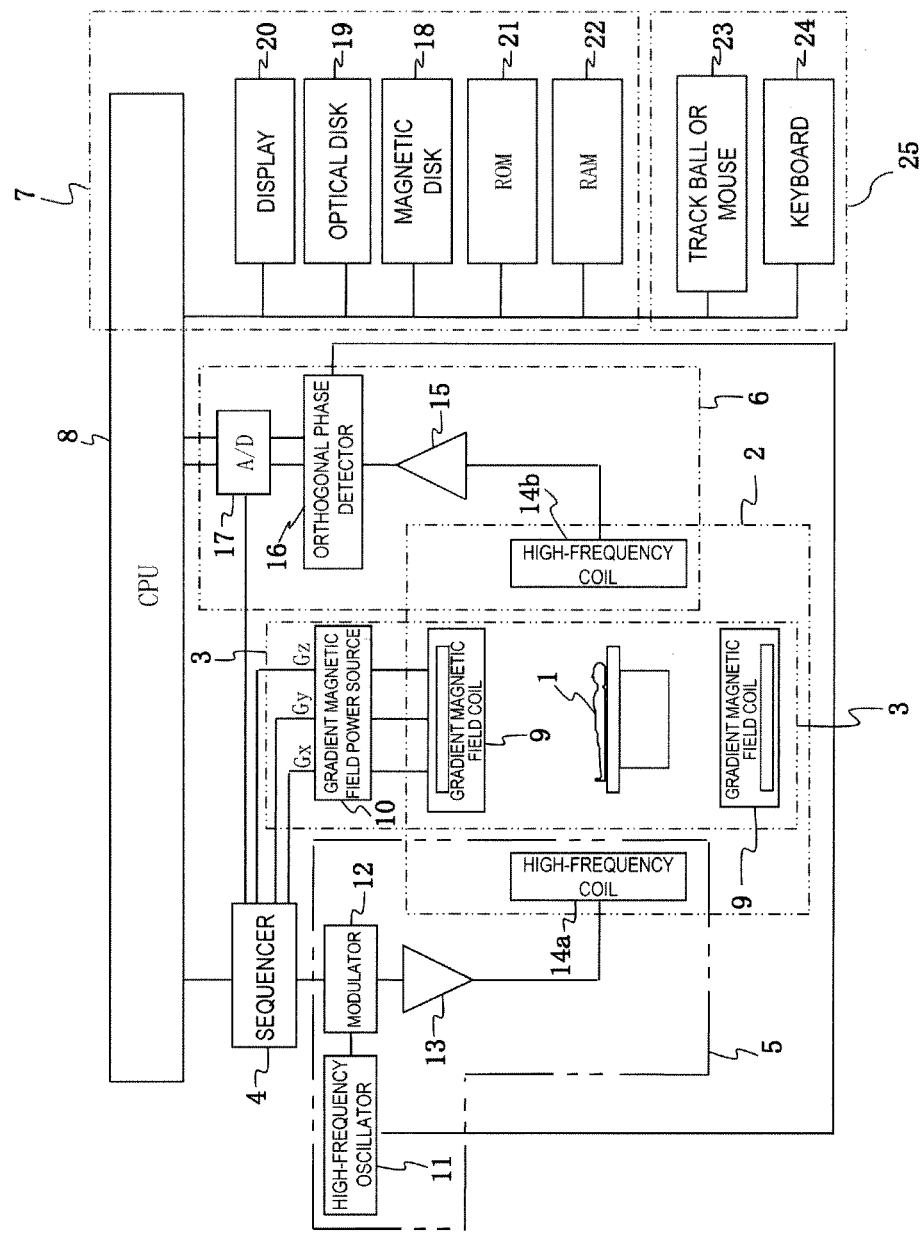
FIG. 1 is a block diagram showing the overall construction of an embodiment of an MRI device according to the present invention.

Embodiments of an MRI device according to the present invention will be described hereunder with reference to the drawings. In all the drawings showing the embodiments of the present invention, constituent elements having the same functions are represented by the same reference numerals, and the repetitive description thereof is omitted.

An example of an MRI device according to the present invention will be described with reference to FIG. 1. FIG. 1 is a block diagram showing the overall construction of the example of the MRI device according to the present invention. The MRI device acquires a tomogram of an examinee by using a nuclear magnetic resonance (NMR) phenomenon, and it is constructed by a magnetostatic field generating system 2, a gradient magnetic field generating system 3, a transmission system 5, a reception system 6, a signal processing system 7, a sequencer 4 and a central processing unit (CPU) 8.

The magnetostatic field generating system 2 generates magnetostatic field uniform in a body axis direction of an examinee 1 or in a direction perpendicular to the body axis direction in a space surrounding the examinee 1, and a permanent magnet type, or normal conduction type or superconduction type magnetic field generator is disposed around the examinee 1.

The gradient magnetic field generating system 3 (gradient magnetic field generator) comprises gradient magnetic field coils 9 wound in three axis directions of X, Y and Z, and gradient magnetic field power sources 10 for driving the respective gradient magnetic field coils 9. The respective gradient magnetic field power sources 10 for the respective coils are driven according to an instruction from the sequencer 4 described later to apply gradient magnetic field Gx, Gy, Gz in the three axis directions of X, Y, Z to the examinee 1. More specifically, a slice selecting gradient magnetic field pulse (Gs) is applied in any one of the directions X, Y, Z to set a slice plane for the examinee 1, and a phase encode gradient magnetic field pulse (Gp) and a frequency encode (or reading) gradient magnetic field pulse (Gf) are applied in the two remaining directions so that position information in the respective directions is encoded to echo signals.

The sequencer 4 is a measurement controller for repetitively applying a radio-frequency magnetic field pulse (hereinafter referred to as "RF pulse") and a gradient magnetic field pulse at a predetermined pulse sequence to control the measurement of echo signals. The sequencer 4 operates under the control of the CPU 8, and transmits various commands for measuring echo signals necessary to reconstruct a tomogram of the examinee 1 to the transmission system 5, the gradient magnetic field generating system 3 and the reception system and controls these systems, thereby controlling the measurement of the echo signals.

The transmission system 5 irradiates atomic nucleus spins of atoms constituting a biomedical tissue of the examinee 1 with an RF pulse so that nuclear magnetic resonance is induced in the atomic nucleus spins, and it comprises a high-frequency oscillator 11, a modulator 12, a high-frequency amplifier 13 and a high-frequency coil 14a at the transmission side. A high-frequency pulse output from the high-frequency oscillator 11 is subjected to amplitude modulation by the modulator 12 at a timing based on an instruction from the sequencer 4, and the amplitude-modulated high-frequency pulse is amplified by the high-frequency amplifier 13 and then supplied to the high-frequency coil 14a disposed in proximity to the examinee 1, whereby the examinee 1 is irradiated with an electromagnetic wave (RF pulse).

The reception system 6 detects an echo signal (NMR signal) discharged through the nuclear magnetic resonance of atomic nucleus spins constituting a biomedical tissue of the examinee 1, and it comprises a high-frequency coil 14b at the reception side, an amplifier 15, an orthogonal phase detector 16 and an A/D converter 17. A responsive electromagnetic wave (NMR signal) of the examinee 1 which is induced by an electromagnetic wave applied from the high-frequency coil 14a at the transmission side is detected by the high-frequency coil 14b disposed in proximity to the examinee 1, and amplified by the amplifier 15. Thereafter, the amplified signal is divided into orthogonal signals of two systems by the orthogonal phase detector 16 at a timing instructed from the sequencer 4, converted to digital amounts by the A/D converter 17 and then transmitted to the signal processing system 7. The digital data of the echo signal will be hereunder referred to as eco data.

The signal processing system 7 has an optical disk 19, an external storage device (storing means) such as a magnetic disk 18, and a display 20 such as CRT. When echo data from the reception system 6 is input to the CPU 8 (calculation processor), the CPU 8 executes calculation processing such as signal processing, and image reconstruction, displays a tomogram of the examinee 1 as a calculation result on the display 20, and records the tomogram in the magnetic disk 18 or the like of the external storage device. Furthermore, the CPU 8 has a memory corresponding to K space therein, and stores the echo data in the memory. The description that the echo data are arranged in the K space means that the echo data are written and stored into the memory. The echo data written in the memory corresponding to the K space are referred to as K-space data.

An operating system 25 inputs various kinds of control information of the MRI device and control information of processing executed by the signal processing system 7, and it comprises a track ball or a mouse 23 and a keyboard 24. This operating system 25 is disposed in proximity to the display 20, and an operator interactively controls various kinds of processing of the MRI device through the operating system 25 while viewing the display 20.

In FIG. 1, the high-frequency coils 14a and 14b at the transmission side and the reception side and the gradient magnetic field coil 9 are disposed in the magnetostatic field space of the magnetostatic field generating system 2 disposed in the space around the examinee 1.

Proton as a main constituent material of the examinee is known as the type of imaging target spins which has been popularly used in the MRI device at present. By imaging the space distribution of a proton density or the space distribution of a relaxation phenomenon of an exciting state, the shape or function of a cephalic part, an abdominal part, four limbs or the like of a human body are two-dimensionally or three-dimensionally imaged.

The PC-MRA method provided to the MRI device according to the present invention will be described.

Figure 2:
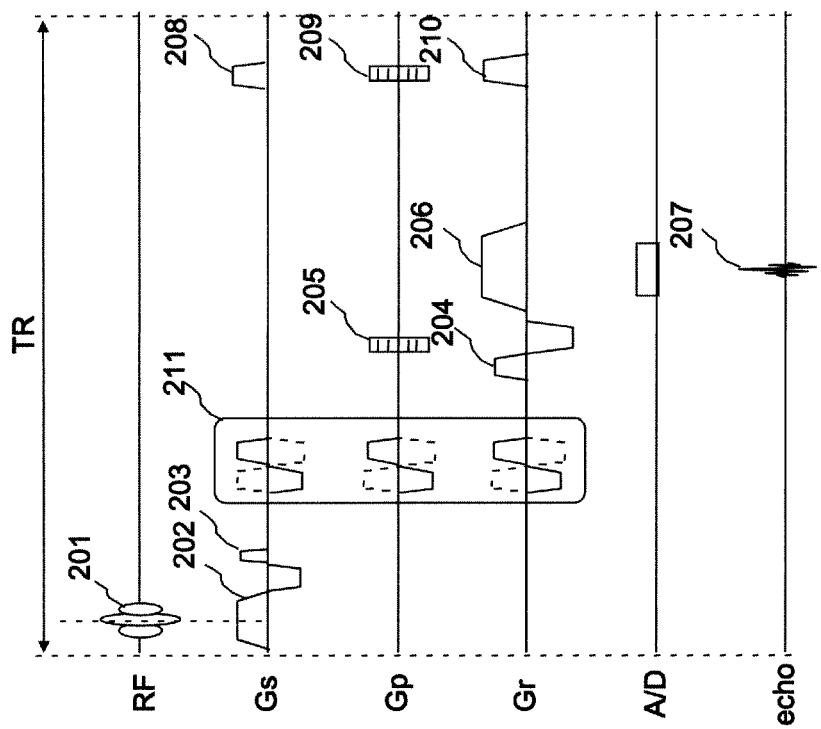
FIG. 2 is a sequence chart of an example of a pulse sequence used for blood vessel imaging of a PC-MRA method.

First, an example of a pulse sequence used for blood vessel imaging of the PC-MRA method will be described on the basis of a sequence chart shown in FIG. 2. FIG. 2 shows a pulse sequence of a two-dimensional gradient echo method by one repeat time (TR), and RF, $G_s$, $G_p$, $G_r$ and Echo respectively represent an RF pulse, slice gradient magnetic field, phase encode gradient magnetic field, frequency encode gradient magnetic field and an axis of an echo signal.

201 represents an RF pulse, 202 represents a slice selecting gradient magnetic field pulse, 203 represents a flow re-phase gradient magnetic field pulse in a slice direction, 204 represents a flow re-phase gradient magnetic field pulse in a frequency encode direction, 205 represents a phase encode gradient magnetic field pulse, 206 represents a frequency encode gradient magnetic field pulse, 207 represents an echo signal, 208, 210 represent spoiler gradient magnetic field pulses, 209 represents a rewind gradient magnetic field pulse, and 211 represents a positive or negative polarity flow encode pulse. The sequencer 4 controls the gradient magnetic field generating system 2, the transmission system 5 and the reception system 6 on the basis of this sequence chart, and controls application of the RF pulse and each gradient magnetic field pulse and the timing thereof, and measurement of echo signals and the timing thereof. Specifically, within one repeat time (TR), the sequencer 4 controls the measurement of the application of each pulse and the measurement of the echo signals as follows.

The RF pulse 201 and the slice selecting gradient magnetic field pulse 202 are simultaneously applied to the examinee, whereby nuclear magnetization is excited in a desired imaging area and transverse magnetization occurs. Subsequently, the flow re-phase gradient magnetic field pulse 203 based on a Gradient Moment Nulling method is applied in the slice direction, thereby cancelling phase dispersion of the transverse magnetization of blood which occurs due to blood stream in the slice direction.

Subsequently, the positive or negative polarity flow encode pulse 211 is applied to the desired axis. FIG. 2 shows an example in which the pulse is applied to each of the three axes. A way of applying the flow encode pulse 211 to each axis will be described in detail later. A solid line represents the flow encode pulse of the positive polarity, and a dashed line represents the flow encode pulse of the negative polarity. The imaging using only the positive-polarity flow encode pulse and the imaging using only the negative-polarity flow encode pulse are repeated to perform blood vessel imaging. The details of the flow encode pulse will be described later.

Subsequently, the phase encode gradient magnetic field pulse 205 and the flow re-phase gradient magnetic field pulse 204 in the frequency encode direction are applied. The phase encode gradient magnetic field pulse 205 is a gradient magnetic field pulse for encoding space information in the phase encode direction to an echo signal. A value of 64, 128, 256, 512 or the like per image is normally selected as the number of phase encodes. The flow re-phase gradient magnetic field pulse 204 based on the Gradient Moment Nulling method in the frequency encode direction is used to cancel the phase dispersion of the transverse magnetization of blood occurring due to blood stream in the frequency encode direction as in the case of the flow re-phase gradient magnetic field pulse 203 in the slice direction.

Subsequently, the frequency encode gradient magnetic field pulse 206 is applied when the echo signal 207 is measured, and used to encode position information in the frequency encode direction to the echo signal. Normally, each echo signal is obtained as a time-series signal comprising sample data of 128, 256, 512 or 1024 in number.

Subsequently, the spoiler gradient magnetic field pulses 208 and 210 and the rewind gradient magnetic field pulse 209 are applied. The spoiler gradient magnetic field pulses 208 and 210 are applied after an echo signal is measured, and used to disperse the phase of transverse magnetization in the applied direction. The rewind gradient magnetic field pulse 209 is a gradient magnetic field pulse whose polarity is opposite to that of the phase encode gradient magnetic field pulse 205, and it cancels a phase encode amount which is applied to the echo signal 207 by the phase encode gradient magnetic field pulse 205. Accordingly, the applied amount of the gradient magnetic field applied to each axis for the repeat time (TR) is fixed irrespective of the repeat time (TR), and the magnetization of the excited area can be led to a stationary state by repeating the pulse sequence of FIG. 2.

The pulse sequence of one repeat constructed by application of each pulse as described above is repeated at only a predetermined repetitive frequency for a short repeat time (TR) while the applied amounts of the phase encode gradient magnetic field pulse 205 and the rewind gradient magnetic field pulse 209 are varied, thereby measuring echo signals whose number is necessary to reconstruct an image. In the foregoing description, the flow re-phase based on the Gradient Moment Nulling method is executed in both the slice direction and the frequency encode direction. However, it is unnecessary to execute the flow re-phase. Furthermore, reduction of the repeat frequency which is implemented by devising a combination pattern of the flow encode pulses will be described later.

(Description of Flow Encode Pulse)

Figure 3:
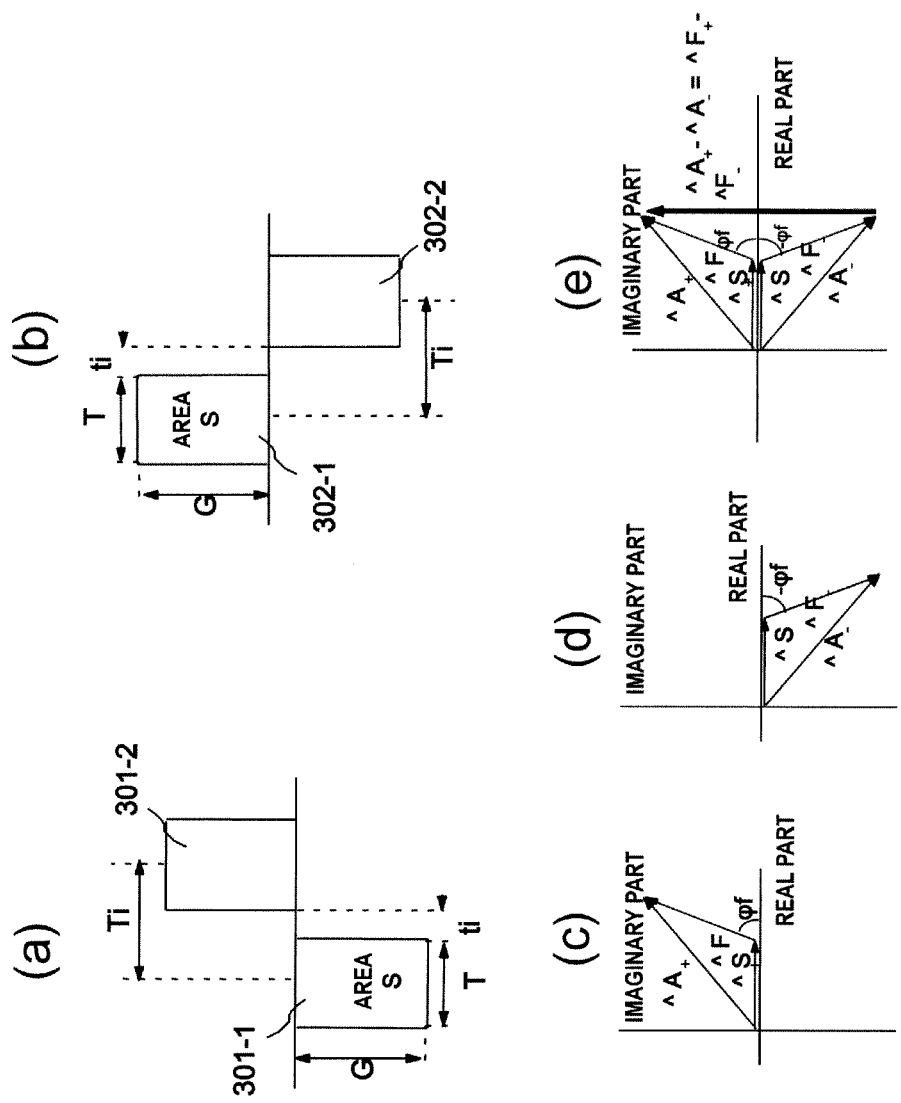
FIG. 3 is a detailed diagram showing a flow encode pulse.

Here, the details of the flow encode pulse will be described with reference to FIG. 3. FIG. 3(a) and FIG. 3(b) respectively show examples of a positive-polarity and negative-polarity flow encode pulses.

The positive-polarity flow encode pulse shown in FIG. 3(a) is a flow encode pulse in which a gradient magnetic field pulse 301-1 having an amplitude of −G, an applied time of T and an applied amount (that is, area) S=−G·T and a gradient magnetic field pulse 301-2 having an amplitude of +G, an applied time of T and an applied amount S=+G·T are configured so that the time interval between the centers thereof is equal to Ti. When the positive-polarity flow encode pulse as described above is applied, the phase of transverse magnetization of blood streaming in the positive direction of the applied direction increases in the forward direction, and the phase of transverse magnetization of blood streaming in the negative direction increases in the negative direction (that is, decreases).

Furthermore, the negative-polarity flow encode pulse shown in FIG. 3(b) has a waveform obtained by reversing the polarity of the positive-polarity flow encode pulse of FIG. 3(a), and it is a flow encode pulse in which a gradient magnetic field pulse 302-1 having an amplitude of +G, an applied time of T and an applied amount S=+G·T and a gradient magnetic field pulse 302-2 having an amplitude of −G, an applied time of T and an applied amount S=−G·T are constructed so that the time interval between the centers thereof is equal to Ti. When the negative-polarity flow encode pulse as described above is applied, the phase of transverse magnetization of blood streaming in the positive direction of the applied direction increases in the negative direction (that is, decreases), and the phase of transverse magnetization of blood streaming in the negative direction increases in the positive direction.

The increase/reduction amount of the phase of transverse magnetization due to both the flow encode pulses is determined dependently on the blood stream rate and the applied amount of the flow encode pulse (hereinafter the applied amount of the flow encode pulse is referred to as flow encode amount). Specifically, a phase shift amount $\phi f$ of the transverse magnetization of blood streaming at a velocity V in the application direction of the flow encode pulse is represented by the mathematical expression (1).

$$\phi f = \gamma \times (+/-) S \times Ti \times V \quad \text{expression (1)}$$

Here, $\gamma$ represents a gyromagnetic ratio, S represents the applied amount (area) of one gradient magnetic field pulse constituting the flow encode pulse as described above, Ti represents the time interval between the mutual centers of two gradient magnetic field pulses constituting the flow encode pulse as described above, and the symbols of + and − represent that the polarity of the flow encode pulse is positive and negative, respectively. The transverse magnetization of a stationary tissue does not suffer phase shift irrespective of the flow encode amount because of V=0.

When the flow encode pulse as described above is applied, a net vector $\hat{A}$ obtained by adding a traverse magnetization vector $\hat{S}$ ($\hat{\;}$ represents a vector) of the stationary tissue and a transverse magnetization vector $\hat{F}$ of blood is represented as shown in FIGS. 3(c), (d) because the transverse magnetization vector $\hat{S}$ of the stationary tissue is invariable.

$$\hat{A}_+ = \hat{S}_+ + \hat{F}_+ = \hat{S} + \hat{F}_+$$

$$\hat{A}_- = \hat{S}_- + \hat{F}_- = \hat{S} + \hat{F}_- \quad \text{expression (2)}$$

The intersecting angle between $\hat{S}_+$ and $\hat{F}_+$ is equal to +$\phi f$, and the intersecting angle between $\hat{S}_-$ and $\hat{F}_-$ is equal to −$\phi f$. A complex difference $\hat{I}$ of both the net vectors thereof is represented as follows.

$$\hat{I} = \hat{A}_+ - \hat{A}_- = \hat{F}_+ - \hat{F}_-$$

$$|\hat{I}| = 2 \times |F| \times |\sin(\phi f)| \quad \text{expression (3)}$$

Here, it may be considered that $|F| = |\hat{F}_+| = |\hat{F}_-|$ and $|F| = (|\hat{F}_+| + |\hat{F}_-|)/2$. That is, it is understood that the complex difference $\hat{I}$ represents only a signal from blood, and the signal intensity thereof is dependent on the flow encode amount and the blood stream rate.

Therefore, in the complex difference image between the image obtained by applying the positive-polarity flow encode pulse to a desired axis and the image obtained by applying the negative-polarity flow encode pulse to the same axis, the signal from the stationary tissue is deleted by the difference concerned, and only the signal from the blood remains, thereby obtaining a blood vessel image.

Furthermore, it is understood from the expression (3) that the absolute value of the complex difference $\hat{I}$ is maximum in the case of $\phi f = \pm \pi/2$. Therefore, when the average flow velocity V of a blood vessel as an imaging target is specified, a flow encode (VENC; Velocity ENCoding) with which the blood vessel concerned is depicted with maximum brightness may be set as follows:

$$VENC = \gamma \times S \times Ti = \pi/(2V) \quad \text{expression (4)}$$

When the blood stream rate is small, the flow encode amount may be increased by increasing S or Ti, and when the blood stream rate is large, the flow encode amount may be reduced by reducing S or Ti.

(Description of Combination Pattern of Flow Encode Pulse)

Next, an efficient combination pattern with respect to the applied axis of the flow encode pulse and the calculation processing based on the combination in the PC-MRA method will be described. When positive and negative flow encode pulses are simply applied to each of the three axes to obtain respective images, and complex difference images of each axis are combined to image blood stream flowing in any direction, in the case of two-dimensional imaging, the repetitive frequency is as follows.

(integration frequency)×(number of phase encodes)× (positive and negative twice)×(directions of three axes)     expression (5)

In the case of three-dimensional imaging, the repetitive frequency is equal to twice the above value (the number of slice encodes).

Furthermore, an integrating measurement is normally used to hold SNR in the imaging operation of two-dimensional one thick slice, and the frequency of the integrating measurement is about 6 to 12 times. These data are subjected to two-dimensional or three-dimensional Fourier transform to create an image. An excessive imaging time is needed to perform the integrating measurement at 6 to 12 times, and a load imposed on a patient increases, so that this method is impractical. Therefore, a method of reducing the repetitive frequency by devising the combination of flow encode pulses to shorten the overall imaging time will be described with reference to FIGS. 4 and 5.

FIG. 4 shows an example of the efficient combination pattern of the flow encode pulse to reduce the repetitive frequency. That is, the orthogonal three axis directions are set to a body axis (FH) direction, an up-and-down (AP) direction and a right-and-left (RL) direction, and a table representing combination patterns (positive polarity is represented by + and negative polarity is represented by −) of the flow encode pulses applied at each time when a blood vessel is depicted in any directions in the imaging of four combination patterns is shown in FIG. 4. Furthermore, FIG. 5 shows K-space data obtained by the combination patterns of the flow encode pulses shown in FIG. 4 and a calculation flow until a final blood vessel image is acquired.

In the case of the first combination pattern (first time (1)), the positive-polarity flow encode pulses are applied in the HF direction and the AP direction and the negative-polarity flow encode pulse is applied in the RL direction to perform imaging, thereby acquiring K-space data 501 and image data 521 obtained by subjecting the K-space data 501 to Fourier transform (IFT). Likewise, in the case of the second combination pattern (second time (2)), the positive-polarity flow encode pulses are applied in the FH direction and the RL direction, and the negative-polarity flow encode pulse is applied in the AP direction to perform imaging, thereby acquiring K-space data 502 and image data 522 obtained by subjecting the K-space data 502 to Fourier transform (IFT). In the case of the third combination pattern (third time (3)), the positive-polarity flow encode pulses are applied in the AP direction and the RL direction, and the negative-polarity flow encode pulse is applied in the HF direction to perform imaging, thereby acquiring K-space data 503 and image data 523 obtained by subjecting the K-space data 503 to Fourier transform (IFT). In the case of the final fourth combination pattern (fourth time (4)), the negative-polarity flow encode pulses are applied in all the three axis directions to perform imaging, thereby acquiring K-space data 504 and image data 524 obtained by subjecting the K-space data 504 to Fourier transform (IFT). Particularly, the image 524 acquired by the fourth combination pattern has a meaning as a reference image because the flow encode pulses having the same polarity are applied along all the axes.

Figure 5:
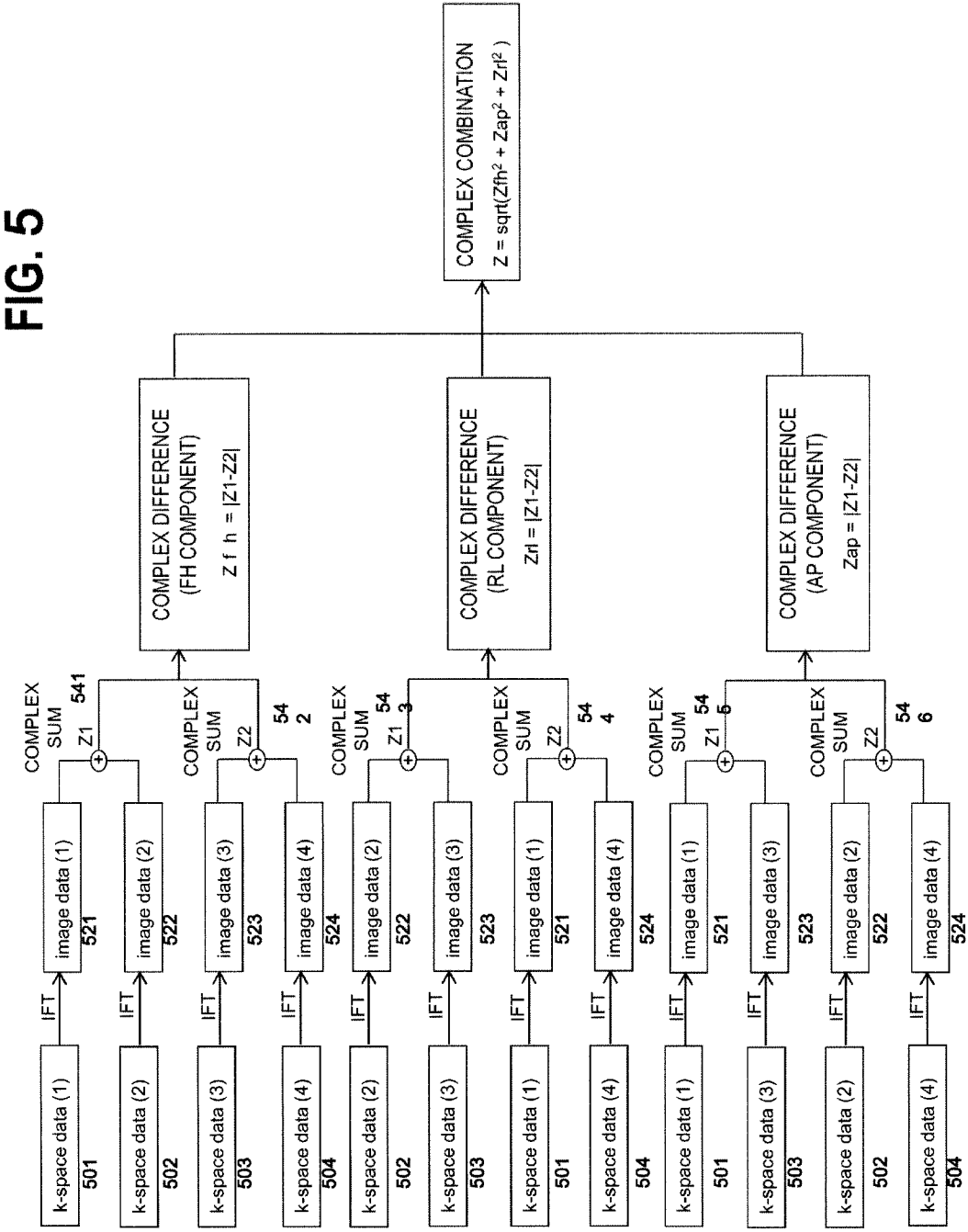
FIG. 5 is a diagram showing a calculation processing flow of obtaining a blood vessel image based on the PC-MRA method according to the present invention.

Next, as shown in FIG. 5, the CPU 8 subjects the image 521 and the image 522 to complex addition to obtain an added image 541. In the added image 541, image data based on the blood flow components in the AP direction and the RL direction are offset with each other by the addition, and only the net vector ($\hat{A}_+^{hf}$) based on the positive-polarity flow encode pulse to the blood flow component in the HF direction remains. Furthermore, the CPU 8 subjects the image 523 and the image 524 to complex addition to obtain an added image 542. In the added image 542, image data based on the blood flow components in the AP direction and the RL direction are offset with each other by the addition as in the case of the added image 541, and only the net vector ($\hat{A}_-^{hf}$) based on the negative-polarity flow encode pulse to the blood flow component in the HF direction remains. Then, the CPU 8 subjects the added image 541 and the conversion image 542 to complex difference to acquire a blood vessel image Zhf based on the blood flow component flowing in the HF direction. On the basis of the same logic, a complex difference image between an added image 543 acquired by executing the complex addition on the image 522 and the image 523 and an added image 544 acquired by executing the complex addition on the image 521 and the image 524 becomes a blood vessel image Zrl based on the blood flow component flowing in the RL direction. Furthermore, a complex difference image between an added image 545 obtained by subjecting the image 521 and the image 523 to complex addition and an added image 546 obtained by subjecting the image 522 and the image 524 to complex addition becomes a blood vessel image Zap based on the blood flow component flowing in the AP direction. Then, the CPU 8 combines the images Zhf, Zrl and Zap in the respective blood flow directions with one another to acquire a composite image Z=sqrt(Zhf$^2$+Zrl$^2$+Zap$^2$). This composite image becomes a blood vessel image depicting blood flows in all directions.

As described above, the repetitive frequency can be reduced by the efficient combination pattern of the flow encode pulses and the calculation processing based on the combination pattern, and in the case of two-dimensional imaging, the repetitive frequency is represented as follows:

(integration frequency)×(number of phase encodes)× (directions(1 to 3)of necessary blood flow information+1)      expression (6)

In the case of three-dimensional imaging, the repetitive frequency is represented as follows:

(integration frequency)×(number of phase encodes)× (number of slice encodes)×(directions(1 to 3)of necessary blood flow information+1)      expression (7)

The repetitive frequency is greatly reduced.

(Description in The Case of Imaging Based on Only One Type of Flow Encode)

Figure 6:
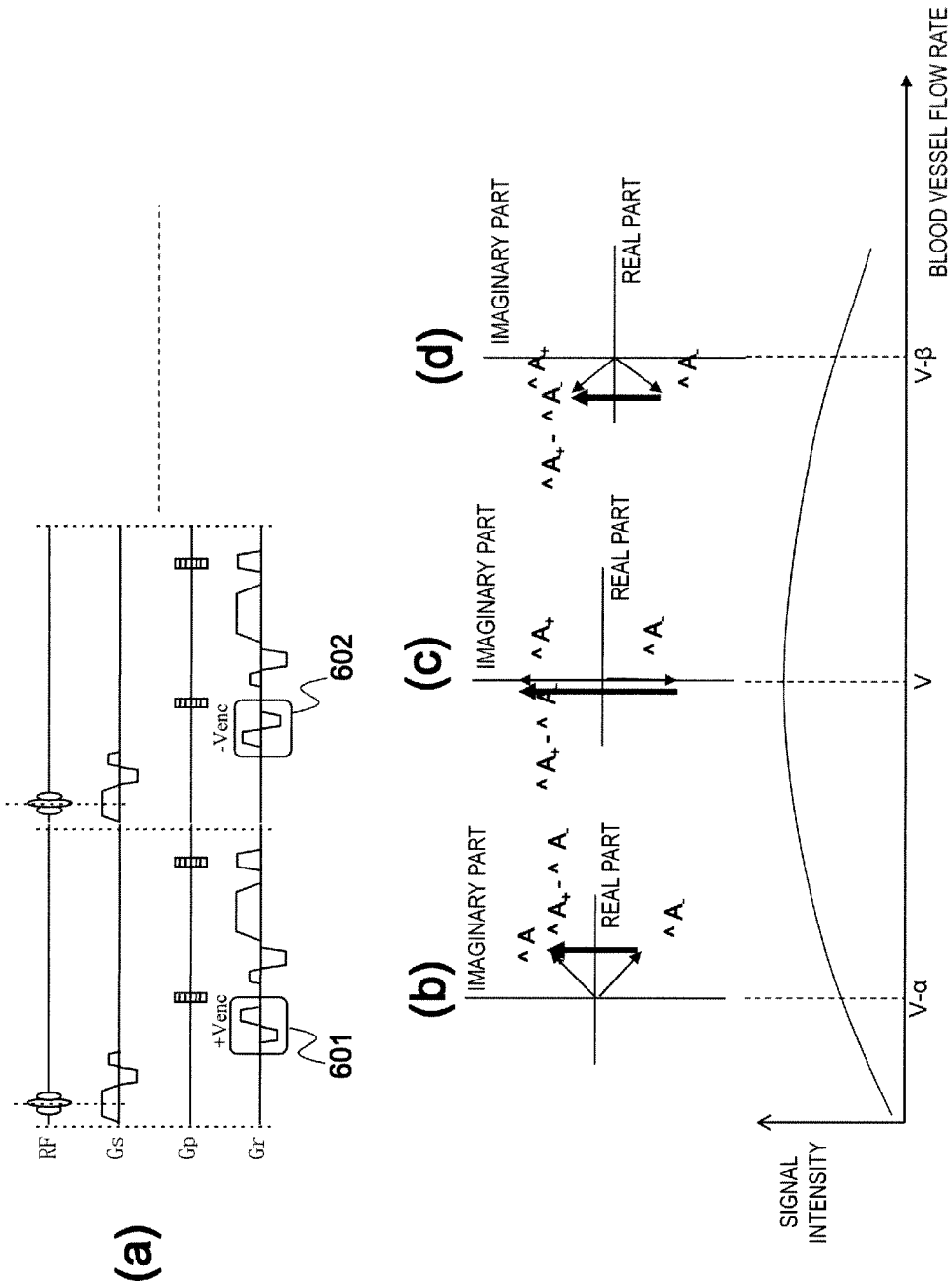
FIG. 6 is a diagram showing the summary of the PC-MRA method based on only one type of flow encode which is optimally matched with an average blood stream rate of a blood vessel as an imaging target.

Next, the PC-MRA method based on only one type of flow encode which is optimally matched with the average blood flow velocity of a blood vessel as an imaging target will be described as a comparative example for promoting understanding of the feature and effect of the present invention with reference to FIG. 6.

In general, plural blood vessels having average blood flow velocities different from an average blood flow velocity in a blood vessel as an imaging target exist in an imaging area. Therefore, in the PC-MRA method based on only one type of flow encode, an imaging target blood vessel is depicted with high brightness, however, other blood vessels are depicted with low brightness and thus each of the blood vessels having the different blood flow velocities does not become any blood vessel image depicted with high brightness.

For example, FIGS. 6(b) to (d) show an aspect of the net vector $\hat{A}$ of each flow velocity of blood flow which is acquired by a pulse sequence containing a positive-polarity flow encode pulse (+VENC; 601) and a negative-polarity flow encode pulse (−VENC; 602) having flow encodes (VENC) matched with the average flow velocity of the blood vessel as the imaging target as shown in FIG. 6(a). In FIGS. 6(b) to (d), the illustration of the transverse magnetization vector of the stationary tissue as shown in FIGS. 3(c) to (d) is omitted. FIG. 6(c) shows a net vector ($\hat{A}_+$, $\hat{A}_-$) of the imaging target blood vessel through which blood having a flow velocity optimally corresponding to the flow encode (VENC) flows. Therefore, in the mathematical expression (1), $\phi f=\pi/2$, the intersecting angle between $\hat{A}_+$ and $\hat{A}_-$ is equal to $\pi$, and the complex difference $\hat{A}$ $(=\hat{A}_+-\hat{A}_-)$ therebetween is maximum. Accordingly, the blood vessel of the imaging target is depicted with high brightness. On the other hand, with respect to a blood vessel having an average flow velocity lower than the average flow velocity of the blood vessel as the imaging target, the flow encode (VENC) is not optimum to the average flow velocity concerned as shown in FIG. 6(b). Therefore, $\phi f$ in the mathematical expression (1) $<\pi/2$ and the intersecting angle between $\hat{A}_+$ and $\hat{A}_-$ is smaller than $\pi$, so that the complex difference $\hat{A}$ $(=\hat{A}_+-\hat{A}_-)$ therebetween is smaller than the complex difference of the imaging target blood vessel of FIG. 6(c).

Accordingly, the blood vessel having the average flow velocity lower than the average flow velocity of the blood vessel as the imaging target is depicted with low brightness. Likewise, with respect to the blood vessel having the average flow velocity higher than the average flow velocity of the imaging target blood vessel, as shown in FIG. 6(d), the flow encode (VENC) is not optimal to the average flow velocity concerned, and thus $\phi f$ in the mathematical expression (1) $>\pi/2$ and the intersecting angle between $\hat{A}_+$ and $\hat{A}_-$ is smaller than $\pi$, so that the complex difference $\hat{A}$ $(=\hat{A}_+-\hat{A}_-)$ therebetween is smaller than the complex difference of the imaging target blood vessel of FIG. 6(c). Accordingly, a blood vessel having an average flow velocity higher than the average flow velocity of the imaging target blood vessel is depicted with low brightness.

From the foregoing description, with respect to the blood vessel imaging based on only one type of flow encode (VENC) which is optimally matched with the average flow velocity of the imaging target blood vessel, only the imaging target blood vessel is depicted with high brightness, and blood vessels of other average flow velocities are depicted with low brightness, so that the brightness of each blood vessel is not uniform in the blood vessel image and thus the image quality is lowered.

Therefore, according to the present invention, plural echo signals having different flow encodes are measured in each of plural phase encodes. Each embodiment of the present invention will be described hereunder in detail.

First Embodiment

Next, a first embodiment of the MRI device and the blood vessel image acquiring method according to the present invention will be described. In this embodiment, a blood vessel image is reconstructed every flow encode by using plural flow encodes, and one blood vessel image is created by combining the blood vessel images of the respective flow encodes, whereby plural blood vessels different in blood flow velocity are depicted with high brightness. For this purpose, plural echo signals having different flow encodes are measured in each of the plural phase encodes. The PC-MRA method of this embodiment will be described with reference to FIGS. 7 to 10 by using a case where one thick slice is imaged.

Description of Summary of Embodiment

First, the summary of this embodiment will be described with reference to FIGS. 7 and 8.

Figure 7:
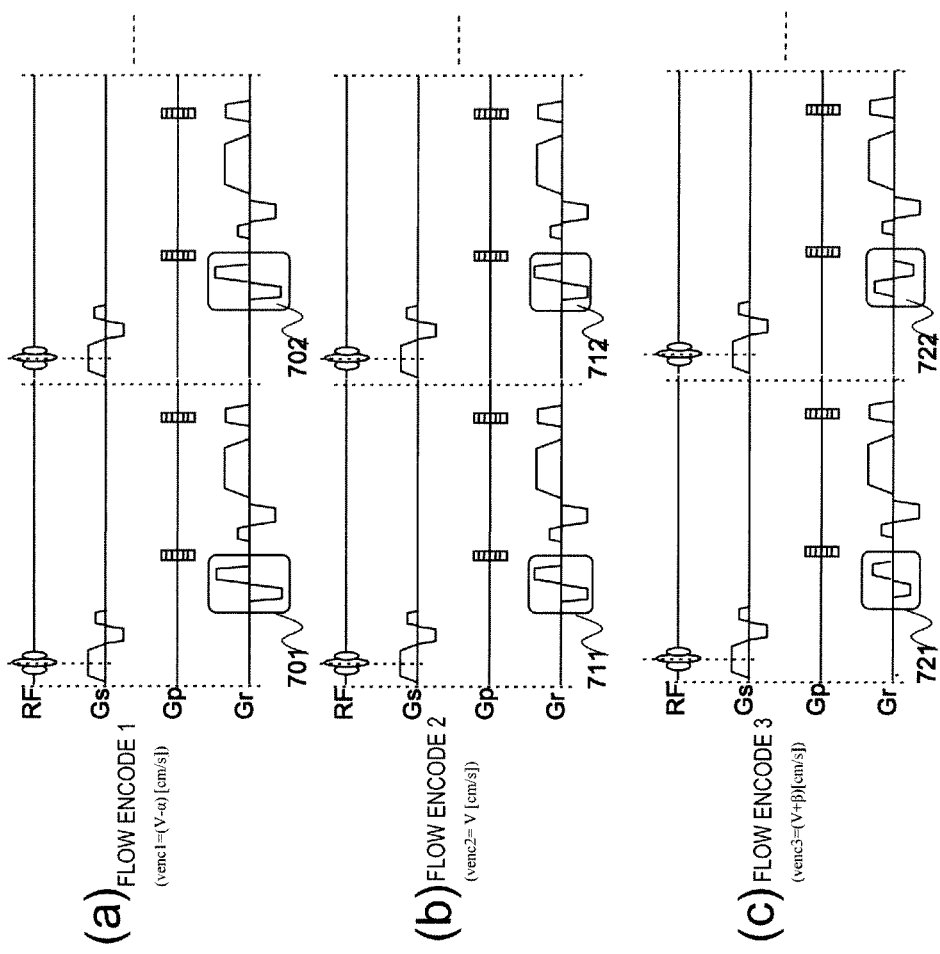
FIG. 7 is a sequence chart of a pulse sequence to which an example of flow encode pulse control of a first embodiment of the present invention is applied.

FIG. 7 is a sequence chart of a pulse sequence to which an example of flow encode pulse control according to this embodiment is applied, and when the average flow velocity of blood flow of a main blood vessel or many blood vessels in one thick slice is represented by V, (a) shows an imaging case using a flow encode (VENC) corresponding to V-α [cm/sec], (b) shows an imaging case using a flow encode (VENC) corresponding to V[cm/sec] and (c) shows an imaging case using a flow encode (VENC) corresponding to V+β[cm/sec]. That is, FIG. 7 shows cases where the average flow velocity V is imaged by VENC2 (711, 712), the low flow velocity V−α is imaged by VENC1 (701, 702) and the high flow velocity V+β is imaged by VENC3 (721, 722). The values of α and β are determined in accordance with a purpose of imaging. For example, V may be set to 50[cm/sec], and α and β may be set to 10[cm/sec]. Furthermore, the flow velocity and the set number of flow encodes are determined in accordance with the distribution of blood flow velocities in the slice, the purpose of imaging and required image quality. When the flow velocity set number is increased to narrow the mutual flow velocity interval, the image quality is enhanced. This embodiment is not limited to the three types of flow encodes, and three or more types of flow encodes may be used.

Figure 8:
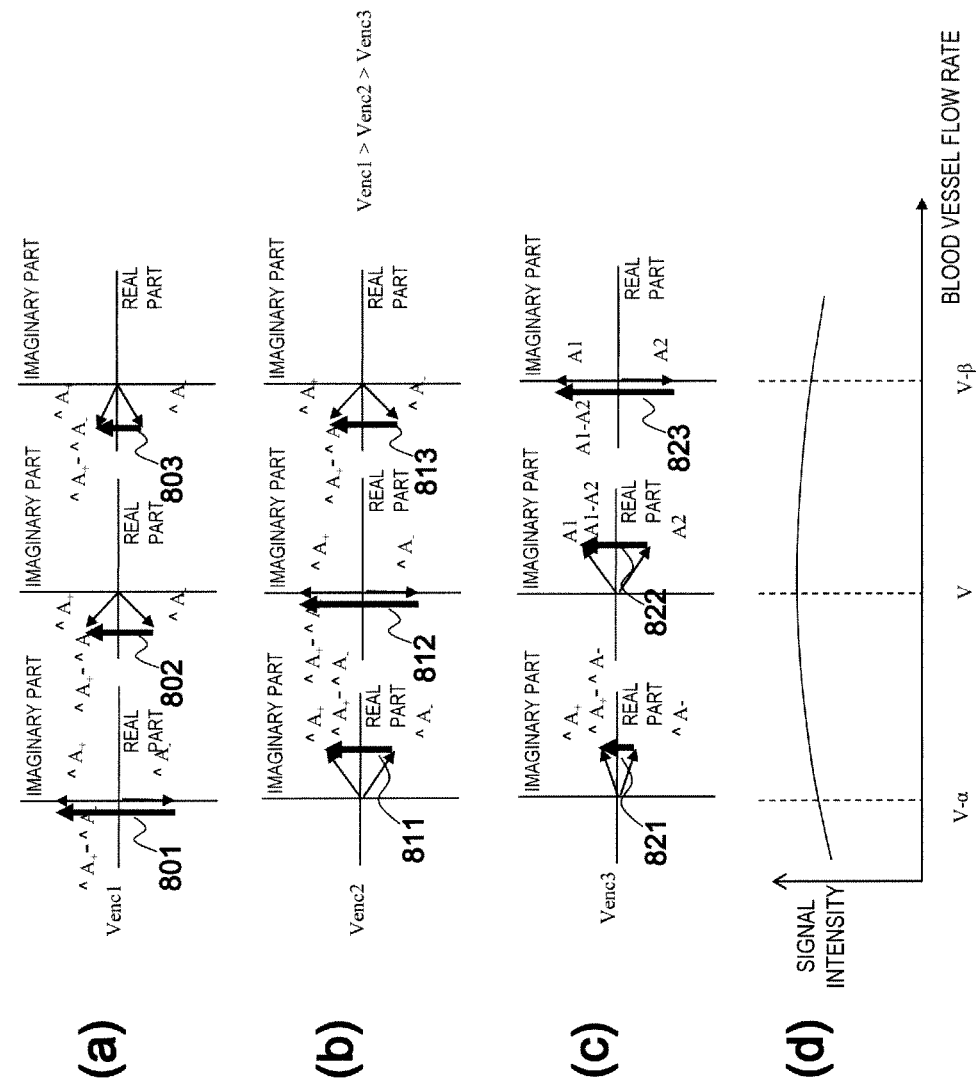
FIG. 8 is a diagram showing an action of the flow encode control of FIG. 7 by a net vector.

Furthermore, FIG. 8 is a diagram showing the action of the flow encode control of FIG. 7 by using a net vector, and shows how three VENCs of FIG. 7 act on blood of each flow velocity by using a net vector every flow velocity corresponding to each VENC. In FIG. 8, the illustration of the transverse magnetization vector of a stationary tissue is omitted.

FIG. 7(a) shows a pulse sequence in which a flow encode 1 (VENC1; 701, 702) corresponding to a blood flow velocity V-α is set to depict the blood of the blood flow velocity V-α with high brightness. From the mathematical expression (4), the amplitude of this VENC1 (701, 702) is set to be larger than VENC2, 3 corresponding to other flow velocities. Imaging is performed every combination pattern shown in FIG. 4 by using this VENC1, and a blood vessel image of VENC1 is acquired through the calculation processing shown in FIG. 5.

FIG. 8(a) shows how VENC1 corresponding to the blood flow velocity V-α acts on the blood of each flow velocity by using net vectors ($\hat{A}_+$ and $\hat{A}_-$). Since VENC1 is optimally set to the blood flow velocity V-α the intersecting angle between the net vectors $\hat{A}_+$ and $\hat{A}_-$ of blood having the flow velocity concerned and blood having flow velocities near to the flow velocity concerned is substantially equal to π. However, the intersecting angle between the net vectors $\hat{A}_+$ and $\hat{A}_-$ of blood having other flow velocities is larger than π.

Accordingly, a complex difference $\hat{A}$ $(=\hat{A}_+-\hat{A}_-)$ 801 of the net vector of the blood of the blood flow velocity V-α is maximum as compared with complex differences 802, 803 of the net vectors of the other blood flow velocities. That is, the blood vessel through which the blood of the blood flow velocity V-α flows is depicted with higher brightness by VENC1 as compared with the blood vessels through which blood of the other blood flow velocities flows.

Next, FIG. 7(b) shows a pulse sequence in which a flow encode 2 (VENC2; 711, 712) corresponding to a blood flow velocity is set in order to depict the blood of the blood flow velocity V with high brightness. From the mathematical expression (4), VENC2 (711, 712) has an intermediate amplitude of VENC1, 3 corresponding to the other flow velocities. As in the case of FIG. 7(a), imaging is performed every combination pattern shown in FIG. 4 by using this VENC2, and a blood vessel image of VENC2 is acquired through the calculation processing shown in FIG. 5.

FIG. 8(b) shows how VENC2 corresponding to the blood flow velocity V acts on the blood of each flow velocity by using the net vectors ($\hat{A}_+$ and $\hat{A}_-$). Since VENC2 is optimally set to the blood flow velocity V, the intersecting angle between the net vectors $\hat{A}_+$ and $\hat{A}_-$ of the blood having the flow velocity concerned and the blood having flow velocities near to the flow velocity concerned is substantially equal to π. However, the intersecting angle between the net vectors $\hat{A}_+$ and $\hat{A}_-$ of blood of other blood flow velocities is smaller (811) or larger (812) than π. Accordingly, complex difference $\hat{A}$ ($=\hat{A}_+-\hat{A}_-$) 812 of the net vector of the blood having the blood flow velocity V is maximum as compared with complex differences 811, 813 of the net vectors of the other blood flow velocities. That is, the blood vessel through which the blood of the blood flow velocity V flows is depicted with higher brightness by VENC2 as compared with the blood vessels through which blood of the other blood flow velocities flows.

Finally, FIG. 7(c) shows a pulse sequence in which a flow encode 3 (VENC3; 721, 722) corresponding to a blood flow velocity V+β is set to depict blood of the blood flow velocity V+β with high brightness, and from the mathematical expression (4), the amplitude of this VENC3 (721, 722) is set to be smaller than those of VENC1, 2 corresponding to the other flow velocities. As in the case of FIG. 7(a), imaging is performed every combination pattern shown in FIG. 4 by using this VENC3, and a blood vessel image of VENC3 is acquired through the calculation processing shown in FIG. 5.

FIG. 8(c) shows how VENC3 corresponding to the blood flow velocity V+β acts on the blood of each flow velocity by using the net vectors ($\hat{A}_+$ and $\hat{A}_-$). Since VENC3 is optimally set to the blood flow velocity V+β, the intersecting angle between the net vectors $\hat{A}_+$ and $\hat{A}_-$ of the blood of the flow velocity concerned and flow velocities near to the flow velocity concerned is substantially equal to π. However, the intersecting angle between the net vectors $\hat{A}_+$ and $\hat{A}_-$ of blood of other blood flow velocities is smaller than π. Accordingly, a complex difference $\hat{A}$ ($=\hat{A}_+-\hat{A}_-$) 823 of the net vector of the blood of the blood flow velocity V+β is maximum as compared with complex differences 821, 822 of the net vectors of the other blood flow velocities. That is, the blood vessel through which blood of the blood flow velocity V+β flows is depicted with high brightness by VENC3 as compared with blood vessels through which blood of the other blood flow velocities flows.

FIG. 8(d) shows a signal intensity distribution of each blood flow velocity in a blood vessel image which is picked up by the PC-MRA method using plural flow encode amounts according to this embodiment. It is understood that as compared with a similar distribution shown in FIG. 6(b), the signal intensity is substantially uniform irrespective of the blood flow velocity.

The measurement of the flow encode corresponding to each flow velocity described above is executed on the basis of each combination pattern of the flow encode pulses shown in FIG. 4. That is, the sequencer 4 performs imaging of the combination pattern of the first flow encode pulse of FIG. 4 every flow encode corresponding to each flow velocity. In the case of examples of FIGS. 7 and 8, imaging is performed by three types of flow encodes. Likewise, the sequencer 4 performs imaging of combination patterns of second to fourth flow encode pulses every flow encode corresponding to each flow velocity. For example, in the example of FIGS. 7 and 8, imaging is performed at the total of (four combination patterns)×(three types of flow encodes)=12 times. Accordingly, when imaging is performed while the number of flow encodes is simply increased, the overall imaging time is extended and thus the load on a patient increases.

Therefore, the integration frequency in the measurement of each flow encode is controlled so that the overall imaging time is not extended. That is, the integration frequency is controlled in accordance with the type of the flow encode so that the measurement frequency=(integration frequency)× (number of flow encodes)×(number of combination patterns) does not increase. Specifically, when the number of flow encodes is increased, the integration frequency is reduced, and when the number of flow encodes is reduced, the integration frequency is increased. Since SNR is dependent on the measurement frequency, in the case of the same measurement frequency, SNR would not vary even when the integration frequency is reduced.

According to this embodiment, the measurement based on the flow encode corresponding to each flow velocity is performed, and thus (the number of flow encodes) increases. Therefore, the overall imaging time is prevented from being extended without varying the (measurement frequency) by reducing the integration frequency in the measurement of each combination pattern of the flow encode pulses. For example, in the case of the conventional imaging based on one type of flow encode, the integration frequency is normally set to six to 12 times to ensure SNR. Therefore, when the number of flow encodes is set to three types, the integration frequency of the measurement based on each flow encode may be set to two to four times. Of course, the integration frequency may be made different among the measurements based on the respective flow encodes.

Finally, the acquired blood vessel images based on the respective flow encodes are combined with one another by using the pulse sequence in FIGS. 7(a) to (c) described above. When the blood vessel images are combined, desired weighting addition may be performed. In this composite image, plural blood vessels having different blood flow velocities are depicted so as to have substantially uniform signal intensity, and thus the image quality of the blood vessel image is enhanced. The details of the image composition will be described later.

Description of Overall Processing Flow is Described Above this Embodiment

Figure 9:
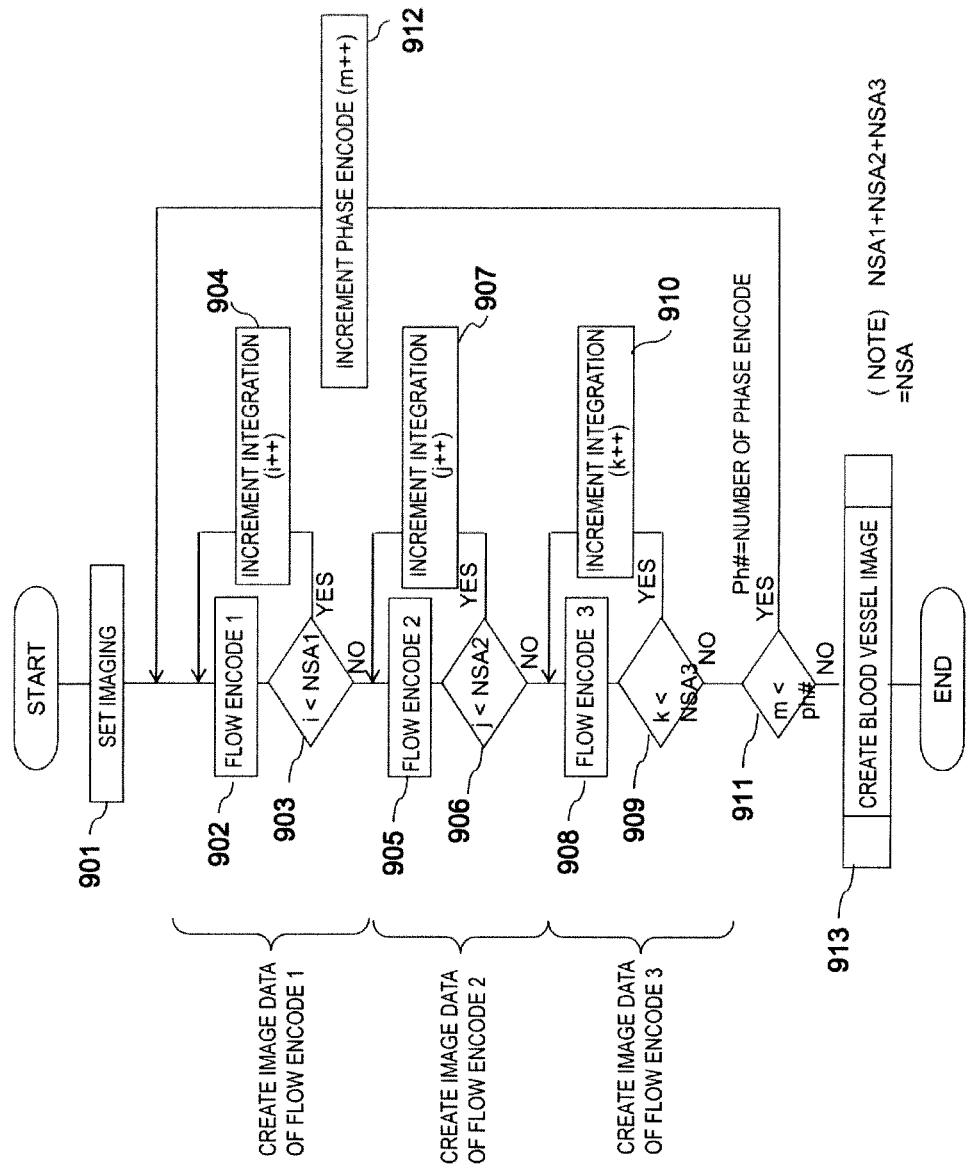
FIG. 9 is a flowchart showing the overall processing flow of the first embodiment according to the present invention.
Figure 10:
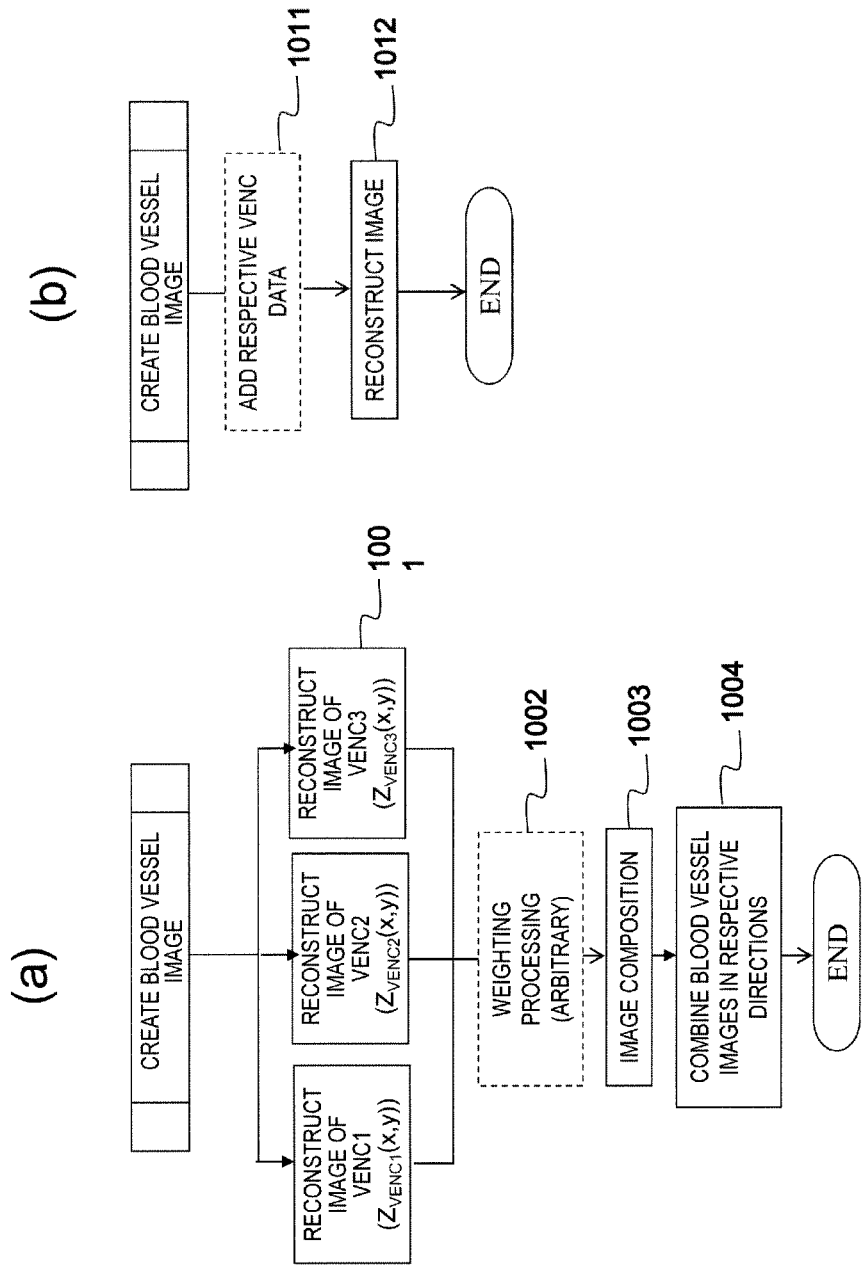
FIG. 10 (a) is a flowchart showing a composite processing flow of a blood vessel image of each flow encode according to the first embodiment of the present invention, and (b) is a flowchart showing a reconstruction processing flow of a blood vessel image according to a second embodiment of the present invention.

Next, the details of the overall processing flow of this embodiment will be described in consideration of the brief summary of this embodiment with reference to FIG. 9. FIG. 9 is a flowchart showing the overall processing flow of this embodiment.

In step 901, setting for blood vessel imaging using the PC-MRA method is executed. An operator first puts an examinee within a measurement space in the magnetostatic field generating system 2. Then, the operator selects blood vessel imaging using the PC-MRA method by using the mouse 23 or the keyboard 24 while viewing various kinds of input screens (GUI) displayed on the display 20, and inputs imaging parameters. With respect to pulse sequences, for example, a pal pulse sequence based on the gradient echo method of FIG. 2 is selected by the operator or the CPU 8, Particularly important imaging parameters in this embodiment are the value of the blood flow velocity of the imaging target and the set number thereof. For example, the operator may input only an average blood flow velocity of a representative blood vessel on the input screen (GUI; blood flow velocity setting unit), and the CPU 8 may set a predetermined number of blood flow velocities obtained by adding or reducing a predetermined value to or from the input average blood flow velocity. Alternatively, the operator may directly input and set plural average blood flow velocities on the input screen (GUI). The CPU 8 determines the flow encode (VENC) corresponding to each blood flow velocity on the basis of the mathematical expression (4) with respect to each of the plural set blood flow velocities. The CPU 8 notifies to the sequencer 4 each imaging parameter which is input and set by the operator or determined by the calculation.

A case where blood vessel imaging corresponding to three types of blood flow velocities V-α, V and V+β is performed as shown in FIGS. 7, 8 will be described hereunder.

In step 902, the pulse sequence based on the flow encode 1 (VENC1) and a phase encode m is executed with respect to each of the combination patterns of the flow encode pulses of FIG. 4. In this flowchart, illustration of the loop of the combination pattern of the flow encode pulses is omitted. The sequencer 4 starts the pulse sequence based on the gradient echo method having VENC1, and controls execution of the pulse sequence of the phase encode m on the basis of each of the flow encode pulse combination patterns, thereby acquiring echo data of the phase encode m in the K-space of VENC1 of each flow encode pulse combination pattern.

When an integration loop parameter (i) is less than a predetermined integration frequency (NAS1) in step 903, the integration loop parameter (i) is incremented in step 904, and the processing returns to step 902 to repeat the pulse sequence of the phase encode m. On the other hand, when the integration loop parameter (i) is equal to the predetermined integration frequency (NAS1), the processing shifts to step 905. Furthermore, the CPU 8 adds the echo data of the phase encode m of each flow encode pulse combination pattern acquired within this integration loop to the echo data of the phase encode m in the K-space of VENC1 of each flow encode pulse combination pattern.

In step 905, the pulse sequence of the flow encode 2 (VENC2) and the phase encode m is executed on the basis of each of the flow encode pulse combination patterns. As in the case of the step 902, the sequencer 4 starts the pulse sequence based on the gradient echo method having VENC2, and controls execution of the pulse sequence of the phase encode m on the basis of each flow encode pulse combination pattern, thereby acquiring echo data of the phase encode m in the K-space of VENC2 of each flow encode pulse combination pattern.

When an integration loop parameter (j) is less than a predetermined integration frequency (NAS2) in step 906, the integration loop parameter (j) is incremented in step 907 and the processing returns to step 905 to repeat the pulse sequence of the phase encode m. On the other hand, when the integration loop parameter (j) is equal to the predetermined integration frequency (NAS2), the processing shifts to step 908. Furthermore, the CPU 8 adds the echo data of each flow encode pulse combination pattern acquired within the integration loop to the echo data of the phase encode m in the K-space of VENC2 of each flow encode pulse combination pattern.

In step 908, the pulse sequence of the flow encode 3 (VENC3) and the phase encode m is executed on the basis of each of the flow encode pulse combination patterns. As in the case of the steps 902, 905, the sequencer 4 starts the pulse sequence based on the gradient echo method having VENC3, and controls execution of the pulse sequence of the phase encode m on the basis of each flow encode pulse combination pattern, thereby acquiring echo data of the phase encode m in the K-space of VENC3 of each flow encode pulse combination pattern.

When an integration loop parameter (k) is less than a predetermined integration frequency (NAS3) in step 909, the integration loop parameter (k) is incremented in step 910 and the processing returns to the step 908 again to repeat the pulse sequence of the phase encode m. On the other hand, when the integration loop parameter (k) is equal to the predetermined integration frequency (NAS3), the processing shifts to step 911. Furthermore, the CPU 8 adds the echo data of each flow encode pulse combination pattern acquired within the integration loop to the echo data of the phase encode m in the K-space of VENC3 corresponding to each combination pattern.

When the phase encode m is less than a predetermined frequency in step 911, the phase encode m is incremented in step 912, and the processing returns to step 902 to execute the pulse sequence of the next phase encode. On the other hand, when the phase encode m is equal to the predetermined frequency, the imaging operation is finished and the processing shifts to step 913.

In step 913, a blood vessel image is created every flow encode, and the blood vessel images of the respective flow encodes are combined with one another. The composite processing of the blood vessel images of the respective flow encode will be described in detail later.

The foregoing description relates to the description on the overall processing flow of this embodiment. The order of the flow encodes in the above processing flow corresponds to the order of VENC1,2, 3. However, the order is not limited to this order, and any order may be used. In the above processing flow, the loop order is set so that the flow encode pulse combination pattern of FIG. 4 is first set and then the integration frequency, the flow encode and the phase encode are set in this order. However, this embodiment is not limited to this order, and any loop order may be used. Furthermore, the case where the blood vessel image of each flow encode is reconstructed after the measurement of all the flow encodes is finished is described above. However, the flow encode loop may be set at the outermost side, and each blood vessel image may be reconstructed at the time point when necessary echo data are prepared every flow encode. Furthermore, plural echo signals having different flow encodes may be measured on the basis of, not all the phase encodes, but each of plural phase encodes.

(Description of Image Composite Processing Flow)

Next, the composite processing of the blood vessel images of the respective flow encodes in step 913 will be described with reference to FIG. 10(a). FIG. 10(a) is a flowchart showing the composite processing flow of the blood vessel images of the respective flow encodes.

In step 1001, the blood vessel image is reconstructed every flow encode i (VENCi). The CPU 8 executes the calculation processing shown in FIG. 5 on the K-space data of each flow encode pulse combination pattern of FIG. 4 to reconstruct a composite blood vessel image (Z) of the respective flow encodes i (VENCi). In FIG. 10(a), the reconstructed blood vessel images of the respective flow encodes (VENC1, VENC2, VENC3) are represented by $Z_{VENC1}(x, y)$ $Z_{VENC2}(x, y)$, $Z_{VENC3}(x, y)$, respectively. In FIG. 10(a), these steps are arranged in parallel, however, any one of parallel processing and serial processing may be used.

Weighting coefficients when the composite blood vessel images of the respective flow encodes are combined with one another are set in step 1002. The CPU 8 sets predetermined weighting coefficients or weighting coefficients input by the operator. When a weighting coefficient for the composite blood vessel image $Z_{VENCi}(x, y)$ of the flow encode i (VENCi) is represented by Ai, the respective weighting coefficients are set so as to satisfy ΣAi=1. Then, the CPU 8 multiplies the corresponding blood vessel image data $Z_{VENCi}(x, y)$ of VENCi by the set weighting coefficient Ai. That is, $Z_{VENCi}(x, y) \leftarrow Ai \times Z_{VENCi}(x, y)$. This step 1002 may be omitted. When omitted, Ai is set to 1/n (n represents the number of flow encodes).

In step 1003, the composite blood vessel images of the respective flow encodes weighted in step 1002 are combined with one another and finally made into one blood vessel image. The CPU 8 sets the square root of the sum of squares of the composite blood vessel images of the respective flow encodes weighted in step 1002 as the final blood vessel image Z(x, y). That is, it is calculated as follows:

$$Z(x, y) = sqrt(\Sigma(Z_{venci}(x, y))^2) \quad \text{expression (8)}$$
$$= sqrt(\Sigma(Ai \cdot Z_{venci}(x, y))^2)$$

The thus-acquired blood vessel images become blood vessel images obtained by depicting plural blood vessels having different blood flow velocities with substantially uniform signal intensity.

The foregoing description relates to the composite processing flow of the blood vessel images of the step 913.

As described above, according to this embodiment, when the blood vessel imaging is executed by the PC-MRA method, plural blood flow velocities are set, the flow encode pulse corresponding to each of the plural blood flow velocities is used to acquire blood vessel images which are obtained by depicting the blood vessels having the corresponding blood flow velocities with high brightness, and the acquired blood vessel images corresponding to the respective blood flow velocities are combined with one another, thereby acquiring a blood vessel image in which plural blood vessels having different blood flow velocities are depicted with substantially uniform signal intensity. As a result, the image quality of the blood vessel image can be enhanced.

Second Embodiment

Next, a second embodiment of the MRI device and the blood vessel image acquiring method according to the present invention will be described.

In the first embodiment, the blood vessel image is reconstructed every flow encode, and the blood vessel images of the respective flow encodes are combined with one another to create one blood vessel image. However, according to this embodiment, K-space data of respective flow encodes are added to one another and then an image is reconstructed, thereby acquiring one blood vessel image.

That is, the echo signals having the different flow encodes are added to one another every phase encode, and then a blood image is reconstructed. Accordingly, the processing flow of this embodiment is basically the same as the processing flow of the first embodiment as described above which is shown in FIG. 9, however, they are different in processing content of the step 913 of creating the final blood vessel image. The description on the same point as the first embodiment is omitted, and only the different point will be described with reference to FIG. 10(b).

FIG. 10(b) is a flowchart showing a reconstruction processing flow of a blood vessel image in this embodiment, and the details of the respective steps will be described hereunder.

In step 1011, K-space data of respective flow encodes i (VENCi) are weighted and added every flow encode pulse combination pattern of FIG. 4. The CPU 8 sets the weighting coefficient of the K-space data of each flow encode i (VENCi) to $a_i$ ($\Sigma a_i = 1$), and calculates a composite K-space data R(j) of each flow encode pulse combination pattern as R(j)=$\Sigma a_i \times$(K-space data (j))$_i$.

In step 1012, the composite K-space data R(j) calculated in step 1011 is regarded as K-space data (j) of FIG. 5, and the same processing is executed. The CPU 8 executes the processing flow shown in FIG. 5 on the composite K-space data R(j) to acquire image data (j) of each flow encode pulse combination pattern. This image data (j) corresponds to image data obtained by adding information of the respective flow encodes i (VENCi). Then, the blood vessel image (Zhf, Zap, Zr1) of each blood flow direction component is acquired. These blood vessel images correspond to blood vessel images obtained by adding the information of the respective flow encodes i (VENCi). Finally, the blood vessel images of the respective blood flow direction components are combined with one another to acquire a blood vessel image representing blood vessels in all the directions. This final blood vessel image also corresponds to a blood vessel image obtained by adding the information of the respective flow encodes i (VENCi).

The foregoing description relates to the processing flow of this embodiment. The K-space data of the respective flow encodes are added and then an image is reconstructed as in the case of this embodiment, whereby the same effect as the first embodiment described above is obtained even when one blood vessel image in which information of respective flow encodes is added is obtained. Furthermore, the processing of reconstructing the blood vessel image of each flow encode is omitted, and thus the processing amount can be reduced as compared with the first embodiment described above.

Third Embodiment

Next, a third embodiment of the MRI device and the blood vessel image acquiring method of the present invention will be described.

In the first embodiment, the operator inputs and sets the average flow velocity of the imaging target blood vessel. However, in this embodiment, the blood flow velocity of a blood vessel is measured in advance, and plural flow encodes are set on the basis of the measurement value. The description of the same point as the first embodiment described above is omitted, and only the different point will be described with reference to FIG. 11.

Figure 11:
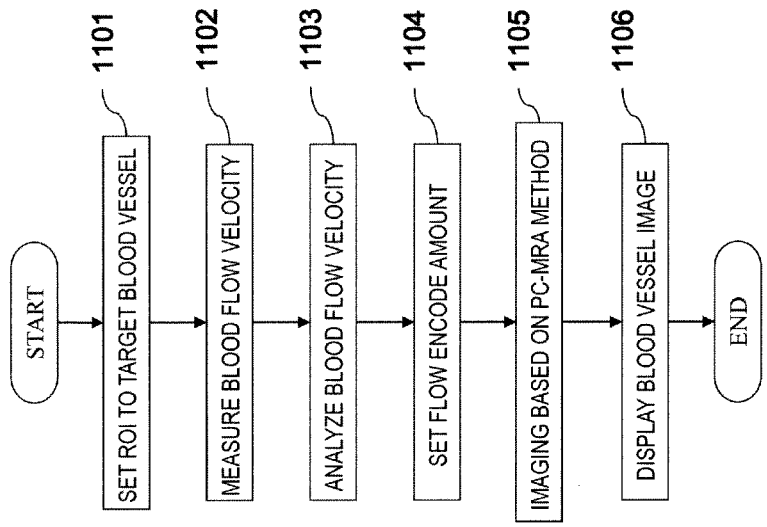
FIG. 11 is a flowchart showing a processing flow of a third embodiment according to the present invention.

FIG. 11 is a flowchart representing a processing flow of measuring a blood flow velocity of a target blood vessel by using the flow velocity measurement of the well-known PC method (for example, Patent Document 2), determining plural encodes on the basis of this measurement value and performing the blood vessel imaging with the plural flow encodes described above by using the PC-MRA method described in the first embodiment. This flowchart is used in both a case where the operator manually executes flow velocity measurement and flow velocity analysis before execution of PC-MRA measurement (hereinafter referred to as manual setting) and a case where the flow velocity measurement and the flow velocity analysis are executed as pre-processing (pre-scan) of the PC-MRA measurement (hereinafter referred to as automatic setting). The details of each step will be described hereunder.

In step 1101, ROI is set to an imaging target blood vessel on a positioning image. The operator sets ROI to the imaging target blood vessel on the positioning image by using the mouse 23 or the like. In the case of the manual setting, this step is skipped.

In step 1102, the pulse sequence based on the well-known PC method is executed to acquire a blood flow velocity distribution image. In the case of the manual setting, the operator starts the pulse sequence of the PC method, and images an imaging area containing an imaging target blood vessel to acquire the blood flow velocity distribution image. In the case of the automatic setting, the CPU 8 determines an imaging area containing ROI set in step 1101, and makes the sequencer 4 image the imaging area concerned as a pre-scan according to the pulse sequence of the PC method.

In step 1103, the analysis of the blood flow velocity is executed. In the case of the manual setting, the operator analyzes the average blood flow velocity of the blood vessel as the imaging target on the basis of the displayed blood flow velocity distribution image. In the automatic setting, the CPU 8 analyzes the blood flow velocity in ROI set in step 1101 on the basis of the acquired blood flow velocity distribution image.

In step 1104, plural flow encodes are set on the basis of the blood flow velocity acquired in step 1103. In the manual setting, the operator inputs and sets the blood flow velocity determined in step 1103 by using the blood flow velocity setting GUI described in the first embodiment, and the CPU 8 sets the flow encode corresponding to each input and set blood flow velocity. In the case of the automatic setting, the CPU 8 determines and sets the flow encode corresponding to the blood flow velocity determined in step 1103.

In step 1105, the blood vessel imaging of the imaging area containing the imaging target blood vessel is executed by the PC-MRA method. The imaging of the imaging area containing the imaging target blood vessel using the PC-MRA method as described in the first embodiment described above is started by the operator in the case of the manual setting or by the CPU 8 in the case of the automatic setting, thereby acquiring the blood vessel image of the imaging area.

In step 1106, the blood vessel image picked up in step 1105 is displayed on the display 20. The foregoing description relates to the processing flow of this embodiment.

Figure 14:
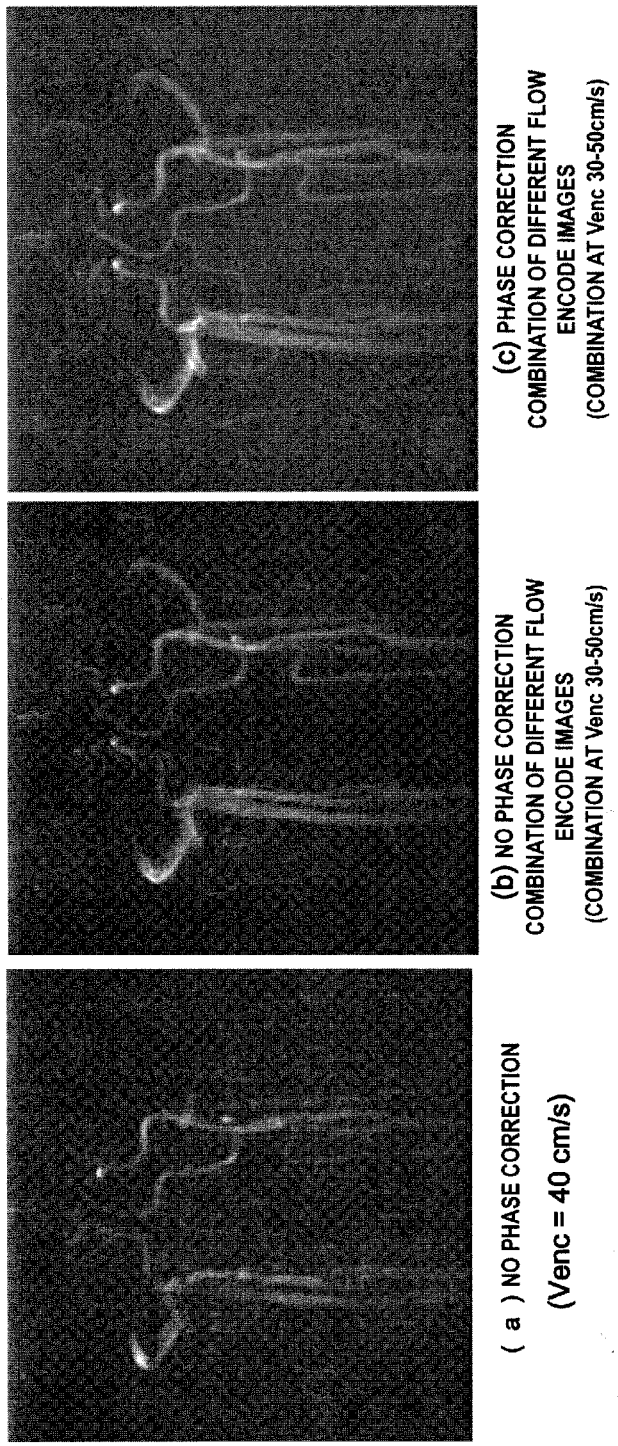
FIG. 14 shows image examples representing specific effects of the third and fourth embodiments of the present invention.

FIG. 14 shows an effect of this embodiment on the basis of a specific image. FIG. 14 shows examples of a conventional imaging result (FIG. 14(*a*)) in a cervical part area and an imaging result in this embodiment (FIG. 14(*b*)). In the cervical part area, a flow encode (40 cm/s) is generally set with a target being set to a carotid artery. In this case, a vertebral artery having a lower flow velocity than the above flow velocity has a lower signal than the carotid artery as shown in FIG. 14(*a*). On the other hand, according to the MRI device of this embodiment, flow encodes (30, 40, 50 cm/s) are set as shown in FIG. 14(*b*). As a result, it is understood that main blood vessels in the carotid artery area (carotid artery, vertebral artery, basilar artery, etc.) are excellently depicted without signal irregularity.

As described above, according to the MRI device of this embodiment, before the blood vessel is imaged, the blood flow velocity of the imaging target blood vessel is acquired by the measurement of the operator or as the pre-scan before the actual imaging operation, and the flow encode is set by using the blood flow velocity concerned. Therefore, the blood flow velocity and the flow encode can be accurately set every patient or every target blood vessel. As a result, a blood flow image having high image quality can be stably acquired.

Fourth Embodiment

Next, a fourth embodiment of the MRI device and the blood vessel image acquiring method according to the present invention will be described. In the first embodiment described above, the image of each combination pattern of flow encode pulses is directly subjected to complex difference to acquire a blood vessel image. When two images are subjected to the complex difference processing while containing a phase error occurring when echo signals are measured, there occurs a case where a proper blood vessel signal is not obtained due to the phase error. Therefore, according to this embodiment, phase correction processing of removing a phase error component from each image is executed before the complex difference processing. The description on the same point as the first embodiment described above is omitted, and only the different point will be described hereunder with reference to FIG. 12.

First, the cause of the phase error will be described. Eddy current occurs due to application of a gradient magnetic field pulse or a cross term effect occurs when gradient magnetic field pulses are simultaneously applied to multiple axes. The eddy current and the cross term effect bring echo signals with a phase error. Such a phase error varies the polarity of the flow encode pulse, and it is not removed, but remains even after the difference is taken between two pick-up image data. Therefore, when the phase error component is not properly removed, the phase error concerned contaminates into the phase of blood and thus degrades the blood vessel depicting function.

The causes of bringing the phase error such as the eddy current, and the cross term effect have space-dependence, however, they spatially vary gently. Therefore, the spatial variation of the phase error which is reflected to the phase of the complex image and based on these causes is also gentle. On the other hand, since the blood vessel is generally thin, the phase variation of the blood vessel portion spatially varies sharply when viewed from the overall area (that is, FOV) of the image. Accordingly, when a gently varying phase component is extracted from the phase of the blood vessel image, the phase component concerned can be regarded as a phase error component. Therefore, in this embodiment, a spatially gently varying phase is extracted from the phase of an image obtained by subjecting a low pass filter to K-space data and executing Fourier transform, and the extracted phase is set as a phase error component. The processing flow of this embodiment will be described hereunder in detail with reference to FIG. 12.

Description of Processing Flow of this Embodiment

Figure 12:
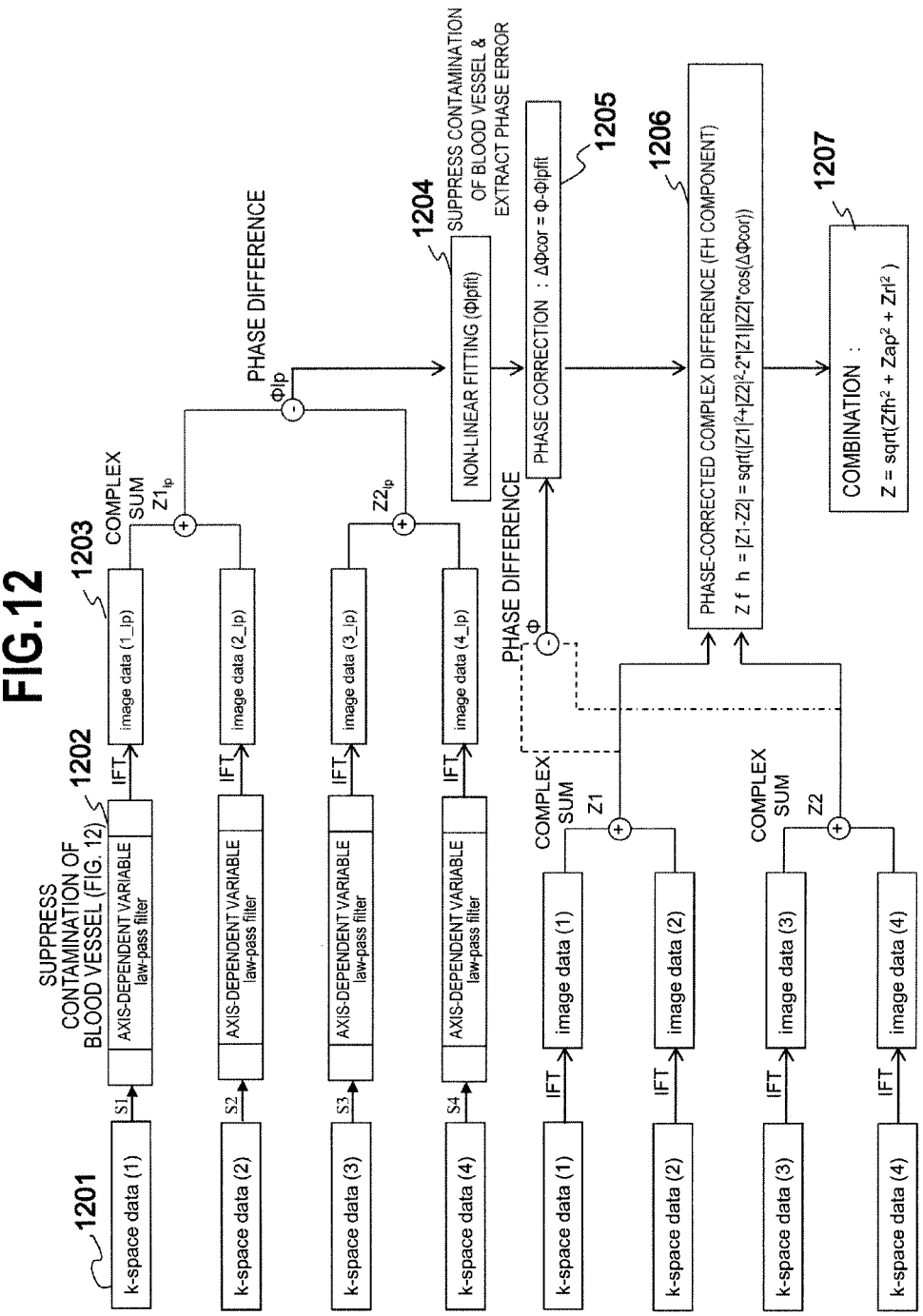
FIG. 12 is a diagram showing a calculation flow according to a fourth embodiment of the present invention.

FIG. 12 shows K-space data of each flow encode pulse combination pattern shown in FIG. 5 and the image thereof, and a calculation flow of reconstructing a blood vessel image of a blood flow component in the HF direction in the calculation flow of the K-space data and the images thereof. The same is applied to the reconstruction of the blood vessel images in the blood flow components in the other AP direction and RL direction.

First, the CPU 8 applies axis-dependent variable low pass filter processing 1202 to K-space data (K-space data (1) to k-space data (4)) (1201) acquired every flow encode pulse combination pattern shown in FIG. 4 (1201). The details of the axis-dependent variable low pass filter processing will be described later.

Subsequently, the CPU 8 executes Fourier transform on the (k-space data (1) to k-space data (4)) (1201) which are subjected to filter processing to acquire complex image data (image data (1_lp) to image data (4_lp)) (1203) thereof.

Subsequently, the CPU 8 acquires a complex sum image $Z1_{lp}$ between the complex image data (image data (1_lp) and the complex image data (image data (2_lp), and acquires a complex sum image $Z2_{lp}$ between the complex image data (image data (3_lP) and the complex image data (image data (4_lp).

Subsequently, the CPU 8 determines a difference $\phi_{|p}$ between the phase of the complex sum image $Z1_{|p}$ and the phase of the complex sum image $Z2_{|p}$.

Subsequently, the CPU 8 subjects the phase difference $\phi_{|p}$ to fitting based on the least square method to acquire a fitting result as a phase error component $\phi_{|pfit}$.

Subsequently, the CPU 8 executes the same processing as the processing of the HF direction component of FIG. 5, that is, acquires complex image data Z1, Z2 from the K-space data (k-space data(1) to k-space data(4)) without applying the axis-dependent variable low pass filter processing.

Subsequently, the CPU 8 determines the difference $\phi$ between the phase of the complex sum image Z1 and the phase of the complex sum image Z2.

Subsequently, the CPU 8 determines a difference ($\Delta\phi_{cor}$) obtained by subtracting phase difference data ($\phi_{|pfit}$) from the phase difference data ($\phi$). Only the phase information of the blood flow accumulated by the flow encode pulses remains in the phase difference ($\Delta\phi_{cor}$) from which the phase error component is removed.

Subsequently, the CPU 8 executes a complex difference processing based on phase correction between the complex sum image Z1 and the complex sum image Z2 by using the phase difference ($\Delta\phi_{cor}$). That is, for Z1=a+jb, Z2=c+jd (j represents imaginary number unit, a, b, c, d represent real numbers), $$|Z1-Z2|=\text{sqrt}((a-c)^2+(b-d)^2) \quad \text{expression (9)}$$

When this expression is rewritten so as to contain the intersection angle between Z1 and Z2, it is expressed as follows.

$$|Z1-Z2|=\text{sqrt}((a^2+b^2)+(c^2+d^2)-2\times\text{sqrt}(a^2+b^2)\times\text{sqrt}(c^2+d^2)\times\cos(\Delta\phi_{cor})) \quad \text{expression (10)}$$

Therefore, the CPU 8 determines the absolute value sqrt($a^2+b^2$) of the complex sum image Z1 and the absolute value sqrt($c^2+d^2$) of the complex sum image Z2, and executes the subtraction of the cosine term using the phase difference ($\Delta\phi_{cor}$) (that is, this is the phase correction of this embodiment), thereby calculating the phase-corrected blood vessel image Zhf in the HF direction. Alternatively, as equivalent processing, the CPU 8 may rotate the phase of any one image of the complex sum image Z1 and the complex sum image Z2 by only the phase difference ($\Delta\phi_{cor}$) and then take the complex difference between Z1 and Z2.

The foregoing description relates to the processing flow of determining the blood vessel image Zhf of the blood flow component in the HF direction, and the blood vessel image Zap of the blood flow component in the AP direction and the blood vessel image Zrl of the blood flow component in the RL direction are also likewise determined.

Finally, the CPU 8 combines the blood vessel images Zhf, Zap and Zrl in the respective directions to acquire the composite blood vessel image Z (1207).

The summary of the processing flow according to the embodiment is described above.

(Description of Axis-dependent Variable Low Pass Filter Processing)

Next, the axis-dependent variable low pass filter processing will be described with reference to FIG. 13.

Figure 13:
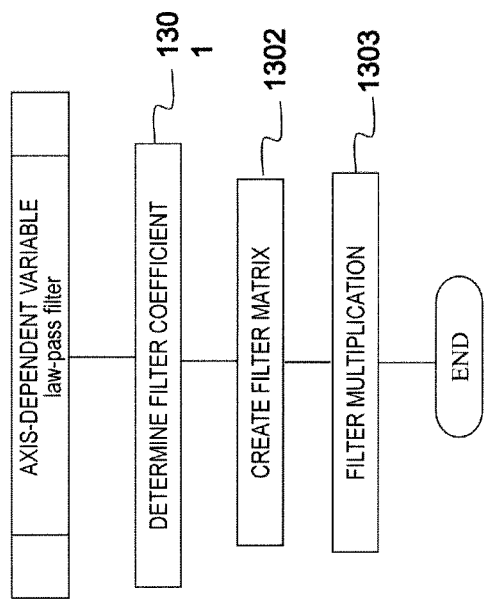
FIG. 13 is a flowchart showing a processing flow of axis-dependent variable low pass filter processing.

FIG. 13 is a flowchart showing the processing flow of the axis-dependent variable low pass filter processing. Each step will be described hereunder in detail.

In step 1301, the CPU 8 sets filter coefficients in accordance with an imaging cross-section and a blood flow direction. That is, the filter shape of the axis-dependent variable low pass filter is determined in accordance with the imaging cross-section and the blood flow direction. For example, the basic shape of the low pass filter can be set to a filter which gently varies like 1→0 from the low area of the K-space to the high area of the K-space, when a blood vessel image of a blood flow component in the normal direction of the imaging cross-section is acquired, the half-bandwidth of the low pass filter is set to (10 to 16)/FOV, and when blood vessel images in blood flow directions other than the normal direction of the imaging cross-section are acquired, the half-bandwidth of the low pass filter can be set to (1 to 2)/FOV. Here, FOV represents the size of the imaging visual field.

In step 1302, the CPU 8 generates a filter matrix on the basis of the half-bandwidth set in step 1301. The filter matrix of each direction is set as follows:

$$Fi(kx,ky)i=HF \text{ or } AP \text{ or } RL$$

In step 1303, the CPU 8 multiplies the K-space data by the filter matrix determined in step 1302, whereby the K-space data are subjected to the low pass filter processing. That is, when the K-space data after the measurement is represented by S(kx, ky) and the K-space data after the low pass filter processing is represented by $S_{|p}$(kx, ky), $$S_{|p}(kx,ky)=S(kx,ky)\times Fi(kx,ky) \quad \text{expression (11)}$$

Then, the CPU 8 changes the low pass filter shape in accordance with the blood flow direction (HF, AP, RL) and executes the low pass filter processing on each K-space data. The filter shape in the axis-dependent variable low pass filter processing may be changed in accordance with the imaging cross-section or the blood flow direction.

The foregoing description relates to the processing flow of the axis-dependent variable low pass filter processing.

FIG. 14 shows an effect of this embodiment on the basis of a specific image. As compared with the image of FIG. 14(*b*) of the first embodiment described above, in the image of FIG. 14(*c*) of this embodiment, it is understood that the intracranial background is reduced, and main blood vessels in the cervical part area (carotid artery, vertebral artery, basilar artery, etc.) are more excellently depicted.

As described above, according to the MRI device of this embodiment, the blood vessel image is acquired by removing the phase error which is caused by the eddy current occurring due to application of the gradient magnetic field pulse and the cross term effect occurring due to the simultaneous application of the gradient magnetic field pulses to multiple axes. When the phase error is removed, the filter shape to be subjected to the K-space data used to extract the phase error is changed in accordance with the axis to which the flow encode in the K-space data concerned is applied, and the phase error and the phase of the blood vessel can be efficiently separated from each other every axis. Accordingly, the complex difference processing based on the phase correction is executed with the phase component derived from the blood flow component on the basis of only the flow encode pulse. Therefore, even a signal from blood having a blood flow velocity which is not optimally suitable to the applied flow encode is corrected in signal intensity by the phase correction, and thus a blood vessel image of high brightness can be acquired over a broader blood flow velocity range as compared with the first embodiment described above.

Fifth Embodiment

Next, a fifth embodiment of the MRI device and the blood vessel image acquiring method according to the present invention will be described. In each of the above-described embodiments, the finally combined blood vessel image is displayed without being modified. However, according to this embodiment, the blood vessel image is subjected to various kinds of blood vessel emphasis filter processing to perform emphasis processing on the blood vessel, thereby creating a blood vessel image which is easily viewable by an operator. The description on the same point as the first embodiment is omitted, and only the different point will be described with reference to FIGS. 15 to 17.

Figure 15:
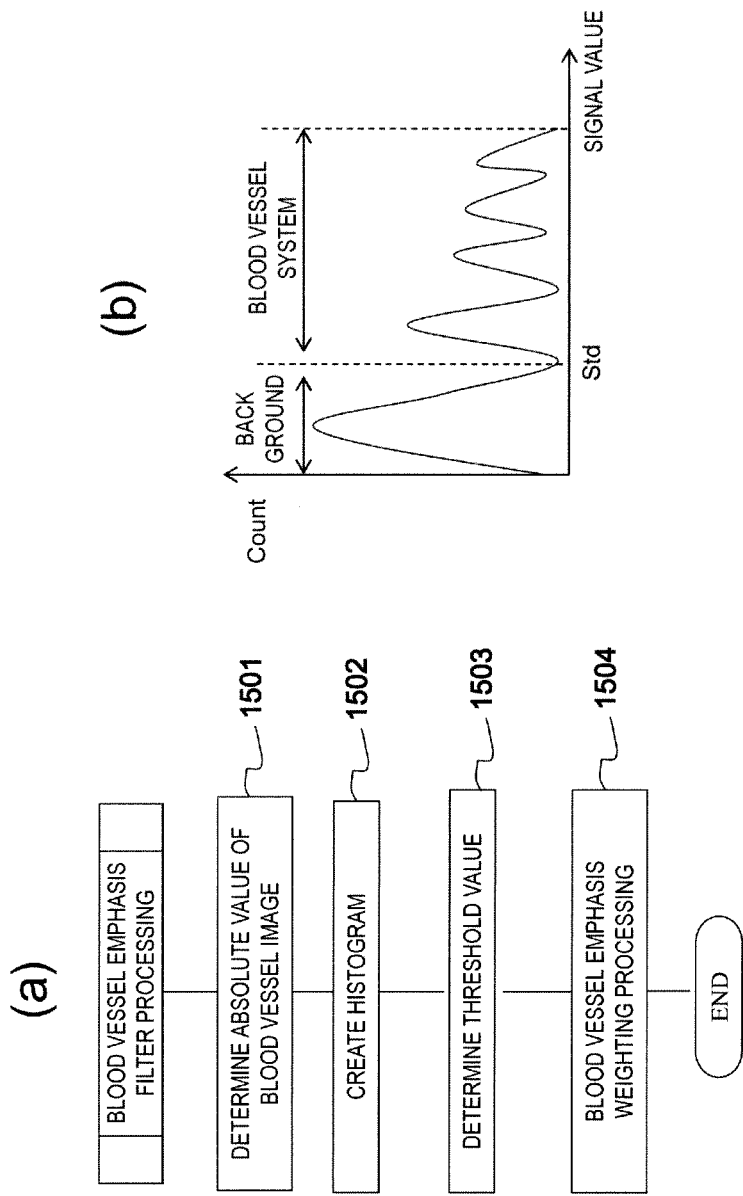
FIG. 15 is a diagram showing a first example of a blood vessel emphasizing filter according to the fourth embodiment of the present invention, wherein (a) is a flowchart showing a processing flow of blood vessel emphasizing filter processing, and (b) is a diagram showing an example of a pixel value histogram of a blood vessel image.

First, the processing flow of a first example of the blood vessel emphasis filter of this embodiment will be described with reference to the flowchart of FIG. 15. The processing flow shown in FIG. 15 is a flowchart of a filter (that is, weighting) processing for emphasizing the signal of the blood vessel, and it is executed in step 1001 of the composite image creating processing flow of FIG. 10 every blood vessel image of the flow encode. Each step will be described hereunder in detail.

In step 1501, the CPU 8 acquires an absolute value image of the blood vessel image. Normally, the absolute value image is presented to the operator. Therefore, in this embodiment, an example in which the blood vessel emphasis filter is applied to the absolute value image will be described. However, in this embodiment, the blood vessel emphasis filter is not limited to applied to the absolute value image, but it may be applied to complex data.

In step 1502, the CPU 8 creates a histogram of respective pixel values of the absolute value image acquired in step 1501. FIG. 15(*b*) shows an example of the histogram. The abscissa axis represents the signal value, and the ordinate axis represents the appearance frequency (Count) of each signal value. The CPU 8 analyzes the histogram, and determines a threshold value (Std) for determining the neighborhood of a pixel value having a high frequency as a background area and discriminating the other area as a blood vessel from the background area. For example, the double of the signal value having the maximum frequency may be set to the threshold value (Std).

In step 1503, CPU regards as a blood vessel pixel a pixel having a signal value which is not less than the threshold value (Std) determined in step 1502, and applies the blood vessel emphasis filer (that is, weighting) processing to pixels having signal values as described above. The following blood vessel emphasis filter is provided, for example.

$$Z(x,y)=(Z(x,y)-Std)^r; \text{ (for } Z>Std) \quad \text{expression (12)}$$

$$Z(x,y)=Z(x,y); \quad \text{(other cases)}$$

Here, r represents a value from 0.1 to 0.3. In the case of the normal processing in which the blood vessel emphasis filer is not applied, r is set to 0.75 to 0.8. By the blood vessel emphasis filter, the signal value in the range of the threshold value (Std)<the signal value<the threshold value (Std)+1 is increased, and the signal value satisfying the threshold value (Std)<<the signal value is suppressed. Accordingly, the brightness of the blood vessel is made uniform by this blood vessel emphasis filter.

Figure 16:
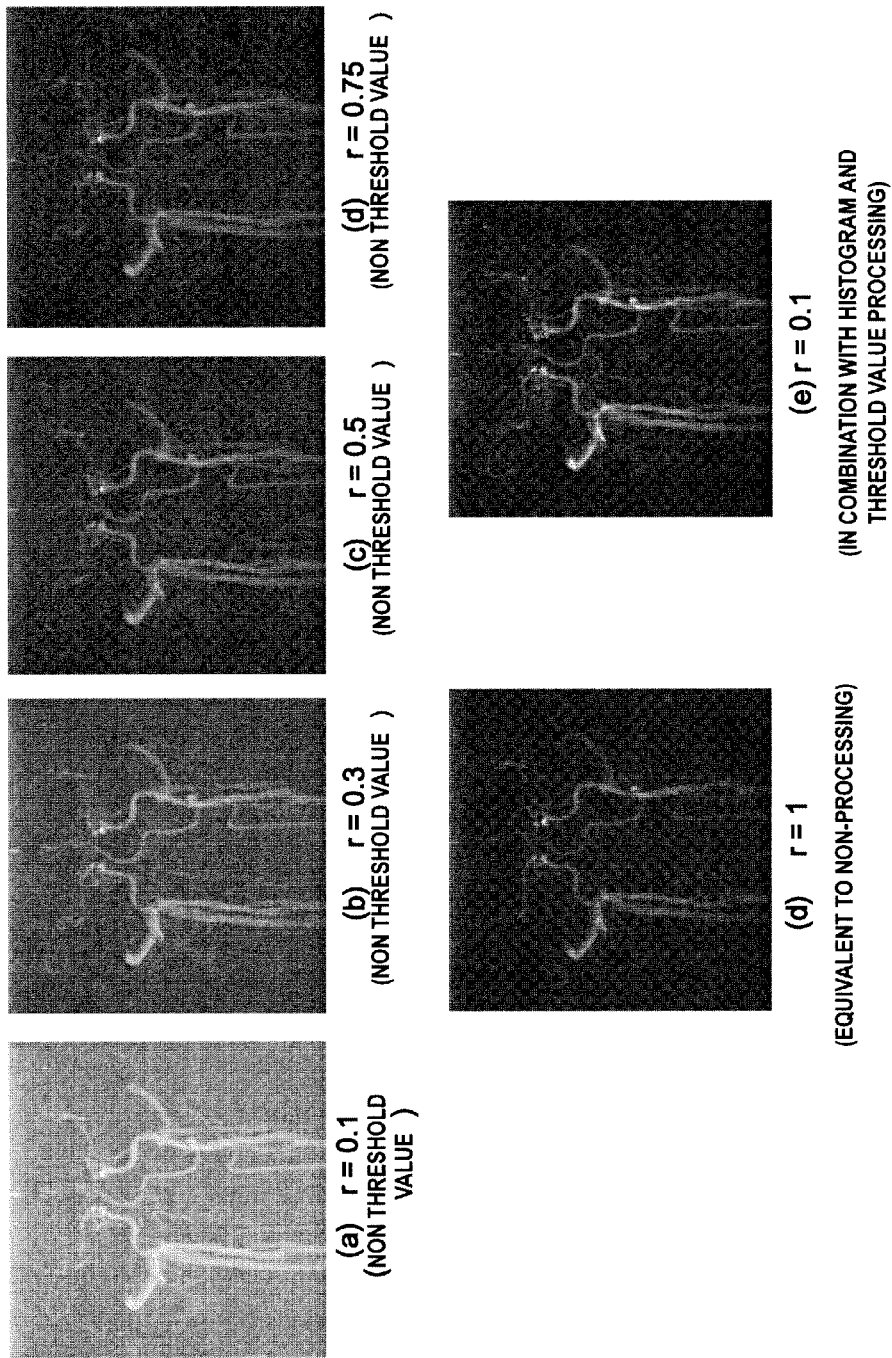
FIG. 16 is a diagram showing an effect of the blood vessel emphasizing filter processing of the fourth embodiment according to the present invention.

The foregoing description relates to the processing flow of the first example of the blood vessel emphasis filter of this embodiment. FIG. 16 shows an example of the effect of the blood vessel emphasis filter of this first example. FIGS. 16(*a*) to (*d*) show examples in which the emphasis filter is conducted on the overall image without analyzing the histogram, and the brightness of the background portion is also increased. On the other hand, it is understood that the histogram analysis provides no unnecessary increase in brightness of the background and emphasizes only blood vessels in the example of in FIG. 16(*e*) in which the blood vessel is extracted and subjected to the emphasis filter.

Next, a second example of the blood vessel emphasis filter of this embodiment will be described. There is a case where an unnecessary signal from a vein is also displayed as a high signal due to the combination of images of different flow encodes, particularly due to contribution of an image of a flow encode sensitive to a low flow velocity. In the blood vessel imaging of the PC-MRA method, the vein signal can be suppressed till the practical level by applying the filter processing of the vein suppression as shown in FIG. 17 by utilizing the property that the blood flow directions of the artery system and the vein system are opposite to each other and the phase polarities thereof are opposite to each other.

The vein suppressing filter processing of the second example will be described hereunder with reference to FIG. 17. The processing flow shown in FIG. 17 is a flowchart showing the blood vessel emphasis filter processing for suppressing a vein signal and extracting only an artery signal, and it is executed in step 1206 of FIG. 12. Each step will be described hereunder in detail.

In step 1701, the CPU 8 acquires a phase difference image $\Delta\phi_{cor}$ (1205) of blood flow direction components i (i=HF, AP, RL) in the second embodiment described above.

In step 1702, the CPU 8 corrects the phase difference image $\Delta\phi_{cor}$ so as to remove the vein signal. For example, $$\Delta\phi_{cor}=0(\Delta\phi_{cor}<0) \quad \text{expression (13)}$$

$$\Delta\phi_{cor}=\Delta\phi_{cor} \quad \text{(other cases)}$$

When this correction is illustrated, the illustration of FIG. 17(*b*) is obtained. That is, the processing of this step corresponds to application of the filter as shown in FIG. 17(*b*) to the phase difference image $\Delta\phi_{cor}$. The cosine term is maximized in the vein portion by the correction of the phase difference image $\Delta\phi_{cor}$ as shown in the mathematical expression (10), and thus the signal from the vein is suppressed.

In step 1703, the CPU 8 executes the calculation of the mathematical expression (10) in the second embodiment described above by using the phase difference image $\Delta\phi_{cor}$ corrected in step 1702 to determine a blood flow direction component image Zhf.

The foregoing description relates to the vein suppression filter processing of the second example. The blood vessel images Zap, Zr1 in the other directions are likewise determined as in the case of the steps 1601 to 1603. FIG. 16(*c*) shows an example of the effect of the second example. A result image acquired through the processing of the second example is shown at the right side while the original image is shown at the left side. It is understood from the right image that the signal of the vein blood vessel is suppressed.

With respect to the second example, the case where the vein signal is suppressed is described above. When the phase difference image $\Delta\phi_{cor}$ is corrected so as to remove the artery signal, an image in which the signal of the artery blood vessel is suppressed can be acquired. For this purpose, the phase difference image $\Delta\phi_{cor}$ may be set as follows, for example.

$$\Delta\phi_{cor}=0(\Delta\phi_{cor}\leq 0) \quad \text{expression (14)}$$

$$\Delta\phi_{cor}=\Delta\phi_{cor} \quad \text{(other cases)}$$

As described above, according to the MRI device according to this embodiment, desired blood vessel emphasis is executed on a blood vessel image picked up according to each of the above-described embodiments, whereby a more easily legible image having higher image quality can be acquired.

DESCRIPTION OF REFERENCE NUMERALS

1 Examinee, 2 magnetostatic field generating system, gradient magnetic field generating system, 4 sequencer, 5 transmission system, 6 reception system, 7 signal processing system, 8 central processing unit (CPU), 9 gradient magnetic field coil, 10 gradient magnetic field power source, 11 high-frequency oscillator, 12 modulator, 13 high-frequency amplifier, 14a high-frequency coil (transmission coil), 14b high-frequency coil (reception coil), 15 signal amplifier, orthogonal phase detector, 17 A/D converter, 18 magnetic disk, 19 optical disk, 20 display, 21 ROM, 22 RAM, 23 track ball or mouse, 24 keyboard, 51 gantry, 52 table, 53 housing, 54 processing unit

The invention claimed is:

1. A magnetic resonance imaging apparatus comprising:
a measurement controller that subjects an examinee to a measurement of an echo signal based on application of a positive-polarity flow encode pulse and a measurement of an echo signal based on application of a negative-polarity flow encode pulse, both flow encodes corresponding to a predetermined flow encode, in respective phase encodes; and
a calculation processor that reconstructs a blood vessel image of the examinee by using the echo signal based on the application of the positive-polarity flow encode pulse and the echo signal based on the application of the negative-polarity flow encode pulse, characterized in that
the measurement controller performs a measurement of plural echo signals having different flow encode absolute values in the respective phase encodes, and
the calculation processor reconstructs the blood vessel image by using the plural echo signals having the different flow encode absolute values; and
the magnetic resonance imaging apparatus further comprising a blood flow velocity setting unit that accepts an input of a desired blood flow velocity, wherein the calculation processor determines a plurality of the flow encodes in accordance with the input and set blood flow velocity, and the measurement controller measures an echo signal of each of the plural determined flow encodes with respect to each of the plural phase encodes.

2. The magnetic resonance imaging apparatus according to claim 1, wherein the calculation processor reconstructs the blood vessel image of the examinee every flow encode.

3. The magnetic resonance imaging apparatus according to claim 2, wherein the calculation processor combines the blood vessel images of the respective flow encodes.

4. The magnetic resonance imaging apparatus according to claim 1, wherein the calculation processor adds the echo signals having different flow encodes every phase encode to reconstruct the blood vessel image of the examinee.

5. The magnetic resonance imaging apparatus according to claim 1, wherein the measurement controller performs pre-scan to acquire blood flow velocity information of blood flowing through a blood vessel of the examinee, the calculation processor determines a plurality of the flow encodes on the basis of the blood flow velocity information acquired through the pre-scan, and the measurement controller measures an echo signal of each of the plural determined flow encodes with respect to each of the plural phase encodes.

6. The magnetic resonance imaging apparatus according to claim 1, wherein the calculation processor performs signal intensity correction of the blood vessel image on the basis of a phase of an image acquired by subjecting the echo signal to a low pass filter.

7. The magnetic resonance imaging apparatus according to claim ein the calculation processor subjects the blood vessel image to a blood vessel emphasis filter to emphasize the brightness of a blood vessel.

8. The magnetic resonance imaging apparatus according to claim 7, wherein the calculation processor acquires an artery-emphasized blood vessel image by using a blood vessel emphasis filter that suppresses pixels having negative phase.

9. The magnetic resonance imaging apparatus according to claim 7, wherein the calculation processor acquires a vein-emphasized blood vessel image by using a blood vessel emphasis filter that suppresses pixels having positive phase.

10. A blood vessel image acquiring method using a magnetic resonance imaging apparatus comprising:
A measurement step that subjects an examinee to a measurement of an echo signal based on application of a positive-polarity flow encode pulse and a measurement of an echo signal based on application of a negative-polarity flow encode pulse, both flow encodes corresponding to a predetermined flow encode in respective phase encodes, and
reconstructs a blood vessel image of the examinee, by using the measured echo signals, based on the application of the positive-polarity flow encode pulse and the echo signal based on the application of the negative-polarity flow encode pulse, characterized in that the measurement step that measures plural echo signals based on application of each flow encode pulse in the respective phase encodes while absolute value of the flow encode is varied;
a reconstructing step that reconstructs a blood vessel image of the examinee by using the echo signals having different absolute values of the flow encode; a blood flow velocity input step that accepts an input of a desired blood flow velocity, wherein a calculation step determines a plurality of the flow encodes in accordance with the input and set blood flow velocity, and the measurement step measures an echo signal of each of the plural determined flow encodes with respect to each of the plural phase encodes; and a display step that displays the blood vessel image.

11. The blood vessel image acquiring method according to claim 10, wherein the reconstructing step has a step that reconstructs a blood vessel image corresponding to the flow encode every flow ode, and a step that combines the blood vessel images of the respective flow encodes to acquire the blood vessel image of the examinee.

12. The blood vessel image acquiring method according to claim 10, wherein the reconstructing step has a step that adds the echo signals having different flow encodes every phase encode, and a step that acquires the blood vessel image of the examinee by an echo signal which is obtained by adding the echo signals having the different flow encodes.

13. The blood vessel image acquiring method according to claim 10, wherein the measurement step has a step that acquires blood flow velocity information of blood flowing through a blood vessel of the examinee, a step that determines a plurality of the flow encodes on the basis of the acquired blood flow velocity information, and a step that measures an echo signal of each of the plural determined flow encodes.

14. A magnetic resonance imaging apparatus comprising: a measurement controller that subjects an examinee to a measurement of an echo signal based on application of a positive-polarity flow encode pulse and a measurement of an echo signal based on application of a negative-polarity flow encode pulse, both flow encodes corresponding to a predetermined flow encode, in respective phase encodes; and
a calculation processor that reconstructs a blood vessel image of the examinee by using the echo signal based on the application of the positive-polarity flow encode pulse and the echo signal based on the application of the negative-polarity flow encode pulse, wherein the measurement controller performs a measurement of plural echo signals by applying different flow encodes around the flow encode of a target velocity in the respective phase encodes, and the calculation processor reconstructs the blood vessel image by using the plural echo signals having the different flow encode absolute values; and the magnetic resonance imaging apparatus further comprising a blood flow velocity setting unit that accepts an input of a desired blood flow velocity, wherein the calculation processor determines a plurality of the flow encodes in accordance with the input and set blood flow velocity, and the measurement controller measures an echo signal of each of the plural determined flow encodes with respect to each of the plural phase encodes.

* * * * *